(12) United States Patent
Butler et al.

(10) Patent No.: US 6,398,562 B1
(45) Date of Patent: Jun. 4, 2002

(54) DEVICE AND METHODS FOR THE APPLICATION OF MECHANICAL FORCE TO A GEL/SENSOR ASSEMBLY

(75) Inventors: Michael J. Butler, San Francisco; Thomas E. Conn, Palo Alto; David M. Liu, Los Altos; Norman A. Parris, Belmont; Michael Reidy, Half Moon Bay; Pravin L. Soni, Sunnyvale, all of CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

(21) Appl. No.: 09/398,984

(22) Filed: Sep. 17, 1999

Related U.S. Application Data
(60) Provisional application No. 60/100,918, filed on Sep. 17, 1998.

(51) Int. Cl.[7] .................................................. H01R 4/58
(52) U.S. Cl. ........................ 439/91; 439/909; 439/725; 439/596
(58) Field of Search ............................ 439/86, 91, 725, 439/909, 596

(56) References Cited

U.S. PATENT DOCUMENTS

| | | | |
|---|---|---|---|
| 5,372,125 A | * | 12/1994 | Lyons ........................ 439/909 |
| 5,735,273 A | * | 4/1998 | Kurnik et al. .............. 128/635 |
| 5,785,040 A | | 7/1998 | Axelgaard |

* cited by examiner

*Primary Examiner*—Tho D. Ta
(74) *Attorney, Agent, or Firm*—Barbara G. McClung; Robins & Pasternak LLP

(57) ABSTRACT

Devices and methods are described for improving the contact of a conductive material, for example, a hydrogel, with a sensor, for example an electrode, by means of using mechanical force to apply the conductive material to the sensor before use of the conductive material and sensor in a sampling device. The device and methods of the present invention improve the sensor response characteristics in transdermal sampling devices placed in operative contact with a skin or mucosal surface of a biological system to obtain a chemical signal associated with an analyte of interest.

20 Claims, 31 Drawing Sheets

Section A-A

Section B

Section A-A

Section B-B

.015 X 45° CHAMFER TYP.

Section A-A

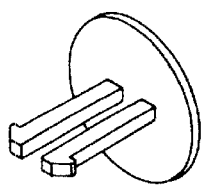
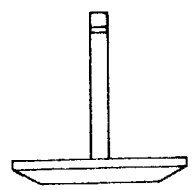
FIG. 21A
FIG. 21B
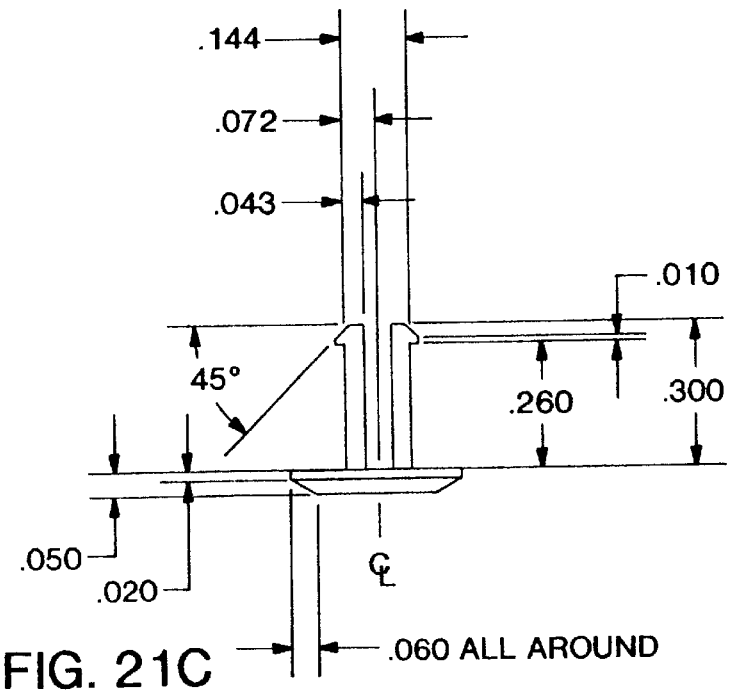
FIG. 21C
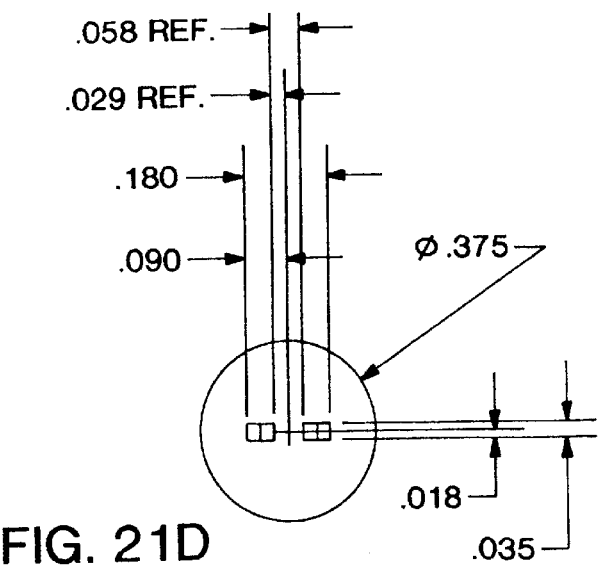
FIG. 21D

Section A-A

DEVICE AND METHODS FOR THE APPLICATION OF MECHANICAL FORCE TO A GEL/SENSOR ASSEMBLY

CROSS-REFERENCE TO RELATED APPLICATIONS

This application is related to U.S. Provisional Patent Application Ser. No. 60/100,918, filed Sep. 17, 1998, from which priority is claimed under 35 USC §119(e)(1), and which application is incorporated herein by reference in its entirety.

FIELD OF THE INVENTION

The invention relates generally to methods for applying pressure to a gel/sensor assembly in order to improve contact between the gel and the sensor apparatus by means of increasing the force applied to the gel when bringing it into contact with the sensor. Further, the invention includes press devices and methods of use thereof. In one embodiment, the invention relates to improving the performance of a gel/sensor assembly used in a device for continually or continuously measuring the concentration of target chemical analytes present in a biological system. One important embodiment of the invention involves applying a force to a collection assembly when bringing it into contact with a sensor/electrode assembly before use in a transdermal monitoring device. The present invention describes that using pressure to improve the interfacial contact between a gel and a sensor substantially increases the sensitivity of the detection system, both in the speed of recovery and overall signal measured.

BACKGROUND OF THE INVENTION

A number of diagnostic tests are routinely performed on humans to evaluate the amount or existence of substances present in blood or other body fluids (including, but not limited to, urine, stool, saliva, and tears). These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by finger prick) for each test, and a determination of the glucose level using an instrument that reads glucose concentrations by electrochemical or calorimetric methods. Type I diabetics should obtain several finger prick blood glucose measurements each day in order to maintain tight glycemic control.

However, the pain and inconvenience associated with this blood sampling, along with the fear of hypoglycemia, has led to poor patient compliance, despite strong evidence that tight control dramatically reduces long-term diabetic complications. In fact, these considerations can often lead to an abatement of the monitoring process by the diabetic. See, e.g., The Diabetes Control and Complications Trial Research Group (1993) *New Engl. J. Med.* 329:977–1036.

In addition, U.S. Pat. No. 5,279,543 to Glikfeld et al. describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose.

Tamada (U.S. Pat. No. 5,771,890, Jun. 30, 1998) teaches a device and method for sampling of substances using alternating polarity. A method for sampling of a substance from a subject is disclosed, as well as, a device for such sampling.

Further, Kurnik, et al., (U.S. Pat. No. 5,735,273, Apr. 7, 1998) disclose a chemical signal-impermeable mask positioned in the electrolyte flow, such that the mask is between a source of chemical signal and a working electrode which senses the chemical signal transported from the source. The patent teaches that by substantially reducing edge effects created by radial transport of chemical signal, it is possible to obtain more accurate measurement of the amount of chemical signal that is transported from a given area of source material.

SUMMARY OF THE INVENTION

In one embodiment, the present invention is directed to a press device to apply mechanical force to improve contact between an ionically conductive gel and a sensor. The device comprises: a first surface on which the gel and sensor are placed, wherein typically the first surface is conformed to hold (or substantially immobilize) a gel and sensor assembly; and a second surface which is conformed to contact the assembly such that the application of mechanical force to the first and second surfaces of the device brings the gel into contact with the sensor, wherein the amount of mechanical force that can be applied is lower than the amount of force that would cause unacceptable deformation of the gel, sensor, or assembly.

In another embodiment, the invention is directed to a method of improving signal detection in a transdermal sampling device having an ionically conductive material in contact with a sensor. The method comprises applying force to bring the tonically conductive material into contact with the sensor, where the amount of force applied is lower than the amount of force that would cause unacceptable damage to the conductive material or sensor.

In an alternative embodiment, the force is applied via mechanical pressure, and the mechanical pressure is applied by a press device as described above.

The methods and devices of the present invention are useful for any sensor application in which the sensor response is limited by inadequate interfacial contact between components (for example, an ionically conductive material (e.g., a gel) and a sensor).

The present invention describes using pressure to improve the interfacial contact between a gel and a sensor, thus substantially increasing the sensitivity of the detection system, both in the speed of recovery and overall signal measured.

These and other embodiments of the subject invention will readily occur to those of skill in the art in light of the disclosure herein.

BRIEF DESCRIPTION OF THE DRAWINGS

FIGS. 21A–D present illustrations of a latch pin involved in creating hinge means to connect the top and bottom components of the press device shown in FIG. 16A.

DETAILED DESCRIPTION OF THE PREFERRED EMBODIMENTS

Figure 1A:
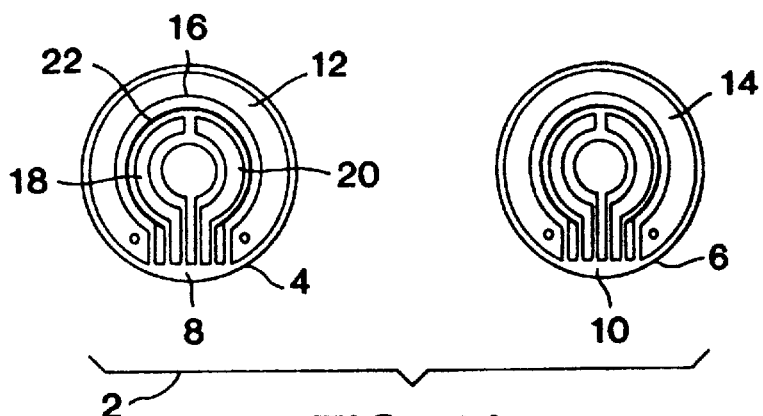
FIG. 1A depicts a top plan view of an iontophoretic collection reservoir and electrode assembly for use in a transdermal sampling device.

Before describing the present invention in detail, it is to be understood that this invention is not limited to particular compositions or biological systems as such and may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a collection insert" includes two or more such inserts, reference to "an analyte" includes a mixture of two or more such analytes, reference to "an electrochemically active species" includes two or more such species, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

In describing and claiming the present invention, the following terminology will be used in accordance with the definitions set out below.

Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) Skin Pharmacology 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) J. Invest. Dermatology 88:88–93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a gel (for example, a hydrogel in the form of a disk or pad). Hydrogels are typically referred to as "collection inserts."

Other suitable collection reservoirs include, but are not limited to, tubes, vials, capillary collection devices, cannulas, and miniaturized etched, ablated or molded flow paths. In a preferred embodiment of the present invention, the collection reservoir is a hydrogel.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across, for example, the surface of skin (e.g., the stratum corneum) or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material. "Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or i"biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986–988), and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J.D., et al. (*Analytical Chemistry* 67(24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" and "collection insert" are used to describe any suitable containment means for containing a sample extracted from a biological system. The reservoir can include a material which is ionically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

As described herein, "mechanical force" is used to apply the gel to the sensor. The amount of mechanical force (for example, the amount of pressure applied) and the period of time for which the mechanical force is applied are dictated by the characteristics of the gel and the sensor. The amount of force and time can be empirically determined by applying pressure to a selected gel/sensor over time and observing at what point deformation of the gel or damage to the sensor occurs. The amount of mechanical force, the time for which the force is applied, and the temperature at which the force is applied are selected to provide an optimal pressure on the gel/sensor interface which results in a desired degree of contact between the hydrogel and the sensor.

"Pressure" is defined as an application of force over an area. "Mechanical force" is defined as a force that is produced or operated by machinery or a mechanism.

"Mechanism" is defined as a system whose parts work together like those of a machine; the arrangement of parts of a machine; or, any system or means for doing something.

General Methods

The present invention relates to methods for applying pressure to a gel/sensor assembly in order to improve contact between the gel and the sensor apparatus by means of increasing the force applied to the gel when bringing it into contact with the sensor. Further, the invention includes press devices and methods of use thereof. Such an application of pressure results in improved sensor response, and thereby improves signal response and the correlation of collected data to the concentration of a target analyte present in a biological system. Further, the devices and methods of the present invention provide a reduction in detection system-to-detection system variability by optimizing sensor response. The device and methods of the invention can be used with any sensor application in which the sensor response is limited by inadequate interfacial contact between components. Laminates, collection assemblies, and other components useful in a sampling device for transdermally extracting and measuring the concentration of a target analyte present in a biological system are described below.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

In one embodiment of the present invention, a sampling device is used for transdermally extracting and measuring the concentration of glucose present in a biological system. A "biosensor" measures the amount of hydrogen peroxide generated from the enzymatic oxidation of glucose and reduction of oxygen. In one configuration, the enzyme that generates the peroxide is contained in a hydrogel, which is placed over a platinum/carbon working electrode. The working electrode converts the peroxide to an electrical signal which is proportional to the amount of glucose. To optimize the performance of this system, the contact between the sensor layer and the hydrogel layer is maximized. The present invention relates to an improved contact of the hydrogel with the sensor by applying a mechanical force to the hydrogel when bringing it into contact with the sensor. By using a mechanical force to increase the pressure used to make contact between the hydrogel and the sensor, the performance of the hydrogel/sensor interface is significantly improved (relative to assembly of the hydrogel/sensor in the absence of applied mechanical force).

Also described herein are exemplary laminates, collection assemblies, and other components useful in a sampling device for transdermally extracting and measuring the concentration of a target analyte present in a biological system. Such sampling devices are generally used for extracting small amounts of a target analyte from the biological system, and then sensing and/or quantifying the concentration of the target analyte. Measurement and/or sampling with the sampling device can be carried out in a continual or continuous manner. Continual or continuous measurements allow for closer monitoring of target analyte concentration fluctuations. In general, the sampling device comprises a biosensor with an electrochemical sensing element, and the sampling device is preferably used to perform continual transdermal or transmucosal sampling of blood glucose.

More specifically, a non-invasive glucose monitoring (sampling) device is used to measure changes in glucose levels in an animal subject over a wide range of glucose concentrations. The sampling method is based on transdermal glucose extraction, and the sensing method is based on electrochemical detection technology. The device can be contacted with the biological system continuously, and automatically obtains glucose samples in order to measure glucose concentration at various selected intervals.

Sampling is carried out continually by non-invasively extracting glucose through the skin of the patient. More particularly, an iontophoretic current is applied to a surface of the skin of a subject. When the current is applied, ions or charged molecules pull along other uncharged molecules or particles such as glucose which are drawn into a collection insert placed on the surface of the skin. The collection insert may comprise any ionically conductive material and is preferably in the form of a hydrogel which is comprised of a hydrophilic material, water and an electrolyte.

The collection insert may further contain an enzyme which catalyzes a reaction of glucose to form an easily detectable species. The enzyme is preferably glucose oxidase (GOx) which catalyzes the reaction between age glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection insert over a given period of time.

When the reaction is complete, the process can be repeated and a subsequent measurement obtained. More specifically, the iontophoretic current is again applied, glucose is drawn through the skin surface into the collection insert, and the reaction is catalyzed in order to create a biosensor current. These sampling (extraction) and sensing operations can be integrated such that glucose is extracted into a hydrogel collection pad where it contacts the GOx enzyme. The GOx enzyme converts glucose and oxygen in the hydrogel to hydrogen peroxide which diffuses to the sensor and is catalyzed by the sensor to regenerate oxygen and form electrons. The electrons generate an electrical signal that can be measured, analyzed, and correlated to blood glucose.

A generalized method for continual monitoring of a physiological analyte is disclosed in International Publication No. WO 97/24059, published Jul. 10 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include, but are not limited to, polyethylene oxide, polyacrylic acid, polyvinylalcohol and related hydrophilic polymeric materials combined with water to form an aqueous gel.

In the above non-invasive glucose monitoring device, a biosensor electrode is positioned against a surface of the hydrogel opposite the surface of the hydrogel which contacts the skin. The sensor electrode acts as a detector which detects current generated by hydrogen peroxide in the redox reaction, or more specifically detects current which is generated by the electrons generated by the redox reaction catalyzed by the reactive surface of the electrode. The details of such electrode assemblies and devices for iontophoretic extraction of glucose are disclosed in International Publication No. WO 96/00110, published Jan. 4, 1996, and International Publication No. WO 97/10499, published Mar. 2, 1997, which publications are also incorporated herein by reference.

In one embodiment the sampling system can have two collection reservoirs which contain, for example, an active collection reservoir, having the GOx enzyme, and a blank collection reservoir (without the GOx enzyme); or, in an alternative, two active reservoirs, i.e., two reservoirs containing the GOx enzyme. In the case of an active collection reservoir and a blank collection reservoir signal can be adjusted by subtraction of the blank reservoir signal from the signal obtained from the active reservoir. In the case of two active collection reservoirs the signals can, for example, be summed and averaged, or a total of the two signals can be used. This signal, for example the detected current, is then used alone or in combination with other factors (for example, glucose concentration at a calibration point, skin temperature, conductivity, voltage, time since calibration of the system, etc.) to provide a glucose concentration value.

In particular embodiments, the detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

A. Exemplary Laminates, Collection Assemblies, and Other Components Useful in a Sampling Device Referring now to FIGS. 1A and 1B, an exemplary iontophoretic collection reservoir and electrode assembly for use in a transdermal sensing device is generally indicated at 2. The assembly comprises two iontophoretic collection reservoirs, 4 and 6, each generally comprising a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described below. A similar biosensor electrode arrangement can be contacted with the conductive medium 10, or the medium may not have an enzyme-sensing means contacted therewith (e.g., in order to provide a blank).

Figure 1B:
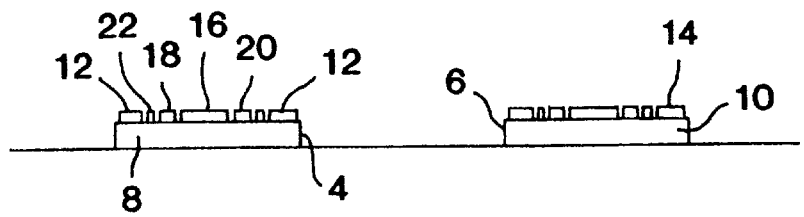
FIG. 1B depicts the side view of the iontophoretic collection reservoir and electrode assembly shown in FIG. 1A.
Figure 2:
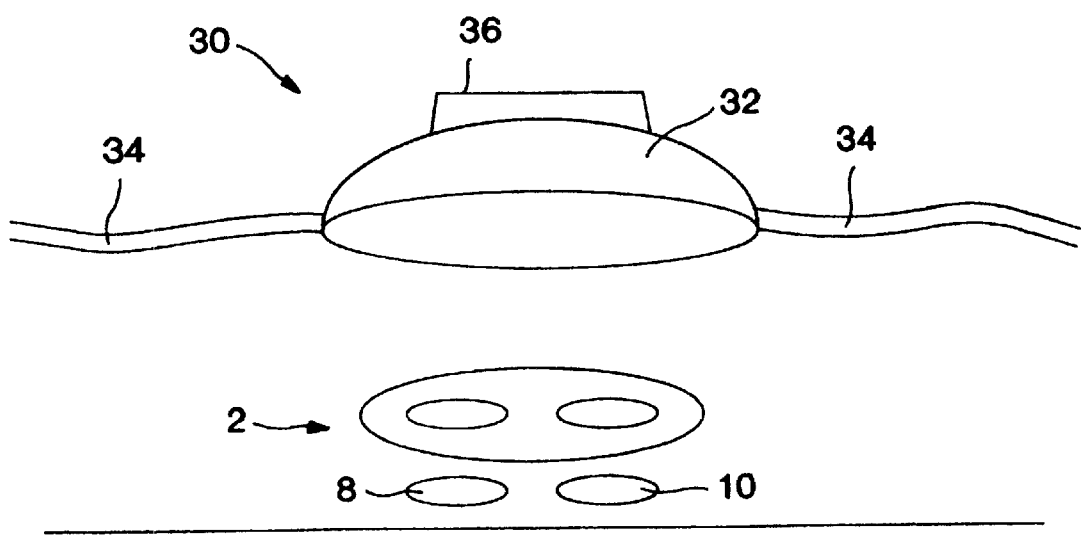
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. FIG. 2 presents one example of a sampling device. The housing can be a plastic case or other suitable structure which preferably is configured to be worn on a subject's arm in a manner similar to a wrist watch. As can be seen, conductive media 8 and 10 (hydrogel pads) are separable from the assembly 2; however, when the assembly 2 and the housing 32 are combined to provide an operational iontophoretic sampling device 30, the media are in contact with the electrodes to provide an electrical contact therewith.

Figure 25:
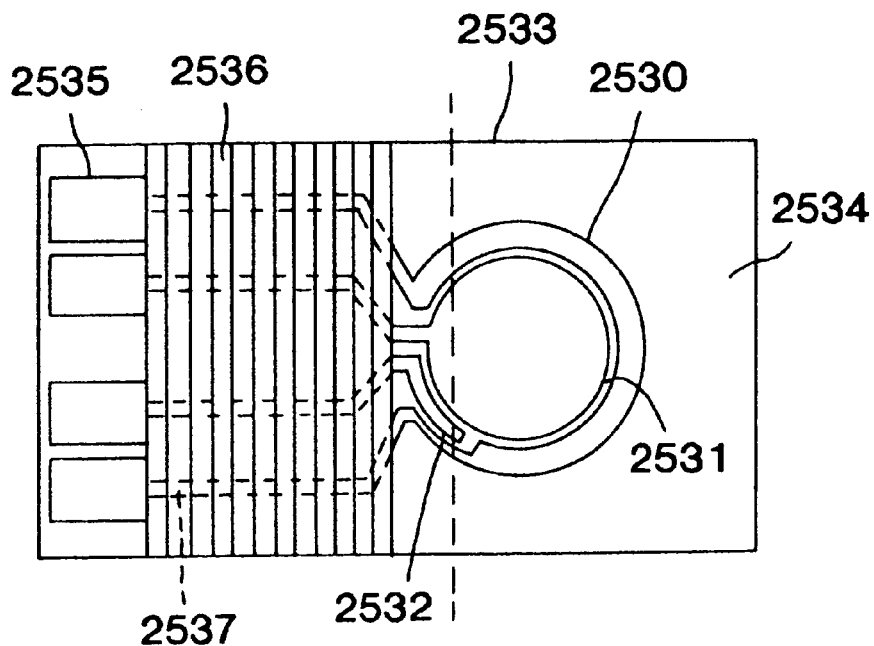
FIG. 25 is a representation of one embodiment of a bimodal electrode design. The figure presents an overhead and schematic view of the electrode assembly 2533. In the figure, the bimodal electrode is shown at 2530 and can be, for example, a Ag/AgCl iontophoretic/counter electrode. The sensing or working electrode (made from, for example, platinum) is shown at 2531. The reference electrode is shown at 2532 and can be, for example, a Ag/AgCl electrode. The components are mounted on a suitable nonconductive substrate 2534, for example, plastic or ceramic. The conductive leads 2537 (represented by dotted lines) leading to the connection pad 2535 are covered by a second nonconductive piece 2536 (the area represented by vertical striping) of similar or different material (e.g., plastic or ceramic). In this example of such an electrode the working electrode area is approximately 1.35 $cm^2$. The dashed line in FIG. 25 represents the plane of the cross-sectional schematic view presented in FIG. 26.
Figure 26:
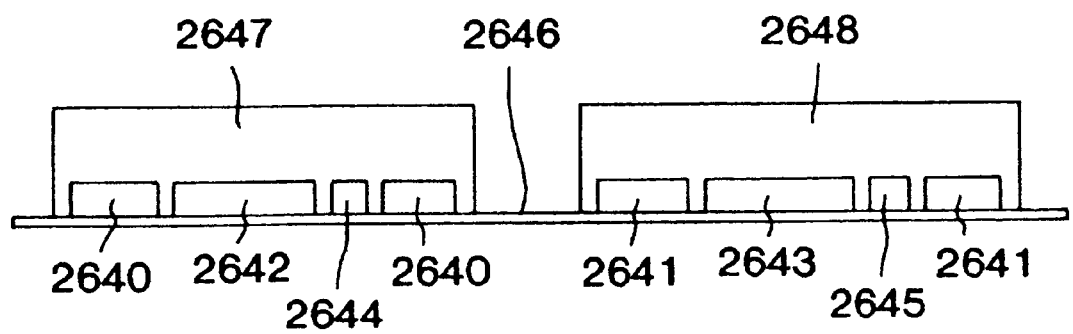
FIG. 26 is a representation of a cross-sectional schematic view of the bimodal electrodes as they may be used in conjunction with a reference electrode and a hydrogel pad. In the figure, the components are as follows: bimodal electrodes 2640 and 2641; sensing electrodes 2642 and 2643; reference electrodes 2644 and 2645; a substrate 2646; and hydrogel pads 2647 and 2648.

In another aspect, the sampling device can operate in an alternating polarity mode using first and second bimodal electrodes (FIG. 26, 2640 and 2641) and two collection reservoirs (FIG. 26, 2647 and 2648). Each bi-modal electrode (FIG. 25, 2530; FIG. 26, 2640 and 2641) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 26, 2644 and 2645; FIG. 25, 2532) and sensing electrodes (FIG. 26, 2642 and 2643; FIG. 25, 2531), as well as, the bimodal electrode (FIG. 26, 2640 and 2641; FIG. 25, 2530) are connected to a standard potentiostat circuit during sensing. In general, practical limitations of the system require that the bimodal electrode will not act as both a counter and iontophoretic electrode simultaneously.

The general operation of an iontophoretic sampling system in this embodiment is the cyclical repetition of two phases: (1) a reverse-iontophoretic phase, followed by a (2) sensing phase. During the reverse iontophoretic phase, the first bimodal electrode (FIG. 26, 2640) acts as an iontophoretic cathode and the second bimodal electrode (FIG. 26, 2641) acts as an iontophoretic anode to complete the circuit. Analyte is collected in the reservoirs, for example, a hydrogel (FIG. 26, 2647 and 2648). At the end of the reverse iontophoretic phase, the iontophoretic current is turned off. During the sensing phase, in the case of glucose, a potential is applied between the reference electrode (FIG. 26, 2644) and the sensing electrode (FIG. 26, 2642). The chemical signal reacts catalytically on the catalytic face of the first sensing electrode (FIG. 26, 2642) producing an electrical current, while the first bi-modal electrode (FIG. 26, 2640) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode must not limit the speed of the reaction at the sensing electrode. In the case of a large sensing electrode, the ability of the counter electrode to source proportionately larger currents is required.

The design of the sampling system provides for a larger sensing electrode (see for example, FIG. 25) than previously designed. Consequently, the size of the bimodal electrode must be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Because the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$ preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like.

Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

To maximize the sensitivity of the sampling device, mechanical force (for example, pressure) is applied to the conductive media (for example, hydrogel pads) for a specified period of time sufficient to provide an optimal pressure on the gel/sensor assembly which results in a desired degree of contact between the hydrogel and the sensor. Using the device described below and illustrated in FIGS. 16–24, such a period of time for the application of pressure may be in the range of about 5–20 seconds, preferably about 10 seconds.

When placing a gel/sensor assembly in a press device of the present invention, the assembly is preferably substantially immobilized (or secured) in the press device during the application of pressure. Examples of immobilization means include, for example, where edges of the gel/sensor assembly firmly contact edges of the press device that prevent substantial movement of the gel/sensor assembly, and, alternatively or in addition, other means may be used, such as, holes in the assembly which pegs (or other retaining means) contact to reduce or prevent movement of the assembly in the press device. An example of a way of securing the assembly is described below and shown in FIG. 20F where two pegs and two edges of the press device are used to immobilize the gel/sensor assembly.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 mA/cm$^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. After a suitable iontophoretic extraction period, one or both of the sensor electrode sets can be activated in order to detect extracted substances including the analyte of interest, or derivative thereof. Operation of the iontophoretic sampling device 30 is preferably controlled by a controller 36 (e.g., a microprocessor), which interfaces with the iontophoretic electrodes, the sensor electrodes, the power supply, as well as optional temperature and/or conductance sensing elements, a display, and other electronics. For example, the controller 36 can include a programmable controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods.

Figure 27:
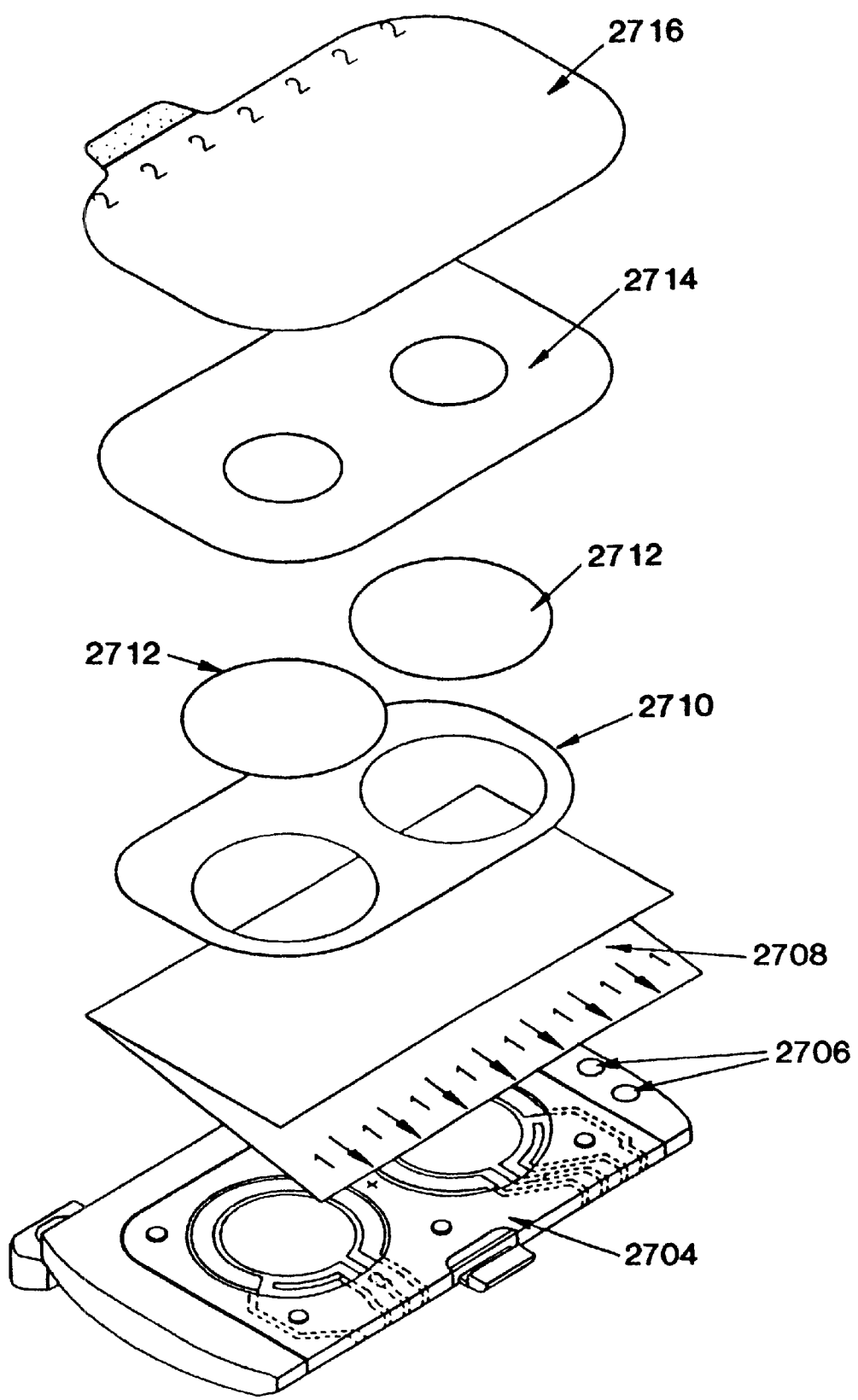
FIG. 27 depicts an exploded view of an embodiment of a gel/sensor-containing collection assembly.

Referring now to FIG. 27, an exploded view of the key components from one embodiment of an iontophoretic sampling system is presented. The sampling system components include, but are not limited to, the following: a sensor-to-tray assembly comprising two bimodal electrode assemblies and a support tray 2704; two holes 2706 to insure proper alignment of the support tray in the sampling device (these holes may also serve to provide proper alignment in a press device of the present invention, as well as, providing means to reduce or prevent movement of such an assembly during the application of mechanical pressure); a plowfold liner 2708 used to separate the sensors from the hydrogels 2712 (for example, during storage); a gel retaining layer 2710; a mask layer 2714 (where the gel retaining layer, hydrogels, and mask layer form a collection assembly, which can, for example, be a laminate); and a patient liner 2716. When applying mechanical pressure to such an assembly, in the practice of the present invention, the plowfold liner is typically removed and the patient liner may be left in place during the application of pressure used to improve contact between the hydrogels and the sensors on the sensor-to-tray assembly.

The components shown in exploded view in FIG. 27 are intended for use in a automatic sampling device which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiment of FIG. 27 will be apparent to those skilled in the art in light of the teachings of the present specification. Following here are further descriptions of exemplary assemblies.

Figure 3:
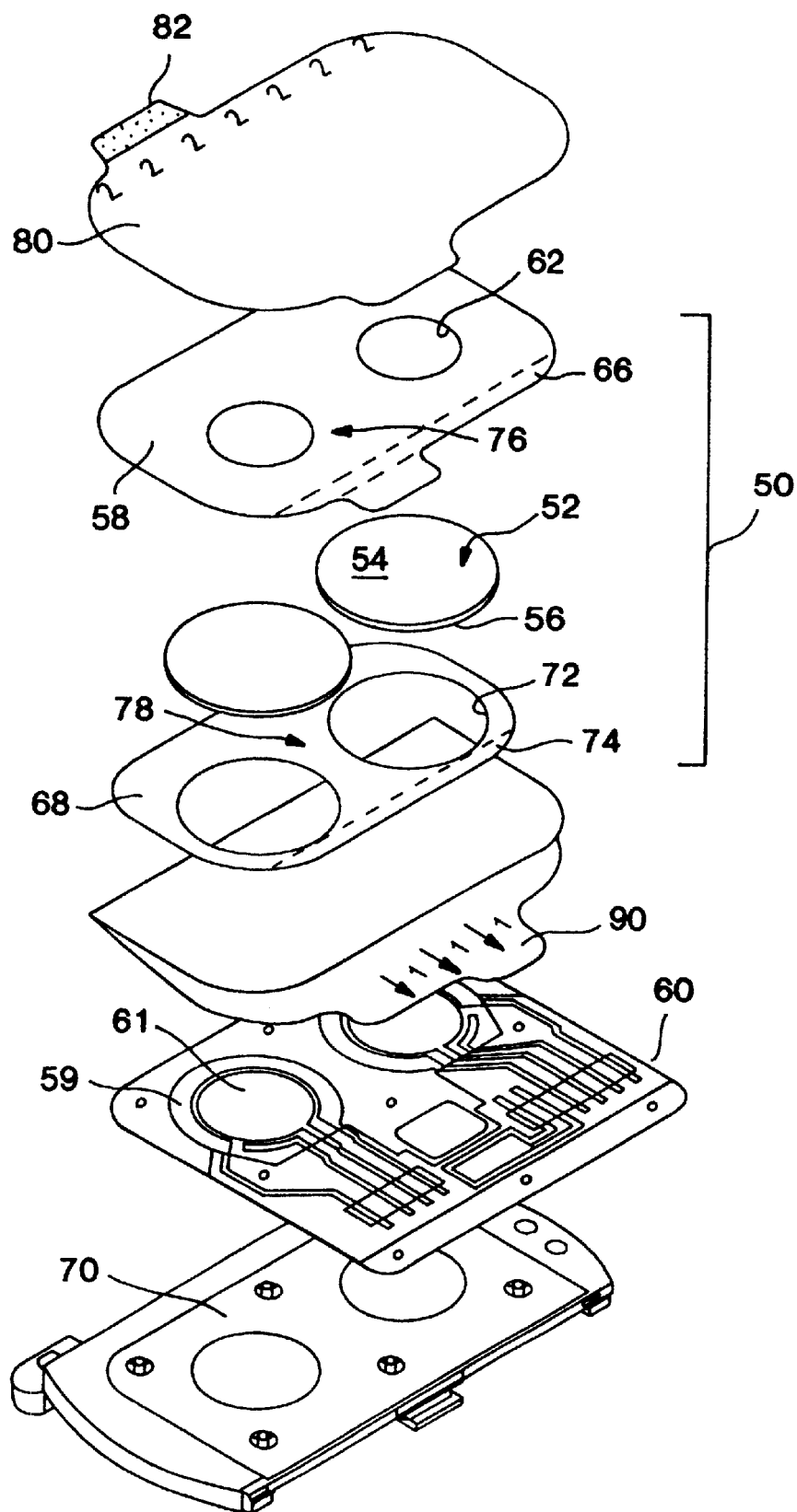
FIG. 3 depicts an exploded view of one embodiment of a gel/sensor collection assembly.

The laminates and collection assemblies described herein are suitable for use as consumable components in an iontophoretic sampling device. Referring now to FIG. 3, one embodiment of a collection assembly for use in such a sampling device is generally indicated at 50. The assembly is aligned with an electrode assembly 60 which includes both iontophoretic 59 and sensing electrodes 61 as described above. A tray 70 is adapted to hold the electrode and collection assemblies in operative alignment, and provides electrical connection between the electrode assembly and control components provided by an associated housing element (e.g., housing 32 of FIG. 2). If desired, the tray 70 can be comprised of a substantially rigid substrate and have features or structures which cooperate and/or help align the various assemblies in the sampling device. For example, the tray can have one or more wells or recesses, and/or one or more lips, rims, or other structures which depend from the substrate, each of which features or structures facilitate registration between the electrode assembly, the collection assembly and the associated components of the sampling device.

The collection assembly 50 includes one or more collection inserts 52 that are comprised of an ionically conductive material. Each collection insert has first and second opposing surfaces, 54 and 56, respectively. The collection insert is preferably comprised of a substantially planar hydrogel disk. The first opposing surface 54 of the insert is intended for contact with a target surface (skin or mucosa), and the second opposing surface 56 is intended for contact with the electrode assembly 60, thereby establishing a flow path between the target surface and the iontophoretic and sensing electrodes. A mask layer 58 is positioned over the first surface 54 of the collection insert. The mask layer is used to inhibit contact between the sensing electrode(s) of the electrode assembly and chemical signal that may be transported in a radial direction from the target surface. The mask layer 58 comprises at least one opening 62 which is sized to allow a detectable amount of chemical signal to reach the sensing electrode, while reducing or preventing entry of chemical signal into the flow path through the insert that has a potential to be transported (e.g., by diffusion) in a radial direction toward an edge of the sensing electrode. As explained in commonly owned U.S. Pat. No. 5,735,273, incorporated by reference herein, this type of mask layer serves to substantially eliminate "edge effect" flow, i.e., the mask prevents chemical signal from contacting the electrode unless the signal flows substantially perpendicular to the surface of the sensing electrode. Accordingly, the opening 62 in the mask layer is sized to expose at least a portion of the first surface 54 of the collection insert. In the particular embodiment depicted in FIG. 3, a border region 66 of the mask layer generally extends beyond the first surface of the collection insert to provide an overhang.

A retaining layer 68 is positioned in facing relation with the second surface 56 of the collection insert 52. The retaining layer has at least one opening 72 which exposes at least a portion of the second surface 56 of the collection insert. Again, in the particular embodiment of FIG. 3, a border region 74 of the retaining layer 68 extends beyond the second surface 56 in order to provide an overhang. The overhangs provided by the mask and retaining layers serve as a point of attachment between the two layers. When these layers are attached to each other at their overhanging portions, a laminate is formed wherein the collection insert is sandwiched between the two layers to provide a three-layer structure. Although the overhangs provided by border regions 66 and 74 are depicted in FIG. 3 as extending along an edge of the mask and retaining layers, the overhangs can, of course, be formed from one or more corresponding tab overhangs (positioned anywhere on the subject layers), one or more corresponding edges (opposite and/or adjacent edges), or can be formed from a continuous overhang which encompasses the collection insert (e.g., an overhang which circumscribes an oval- or circular-shaped insert, or an overhang which surrounds all sides of a square-, rectangular-, rhomboid-, or triangular-shaped insert).

The one or more openings 62 in the mask layer, and the one or more openings 72 in the retaining layer can have any suitable geometry which is generally dictated by the shape of the collection insert 52 and/or the shape of the iontophoretic and sensing electrodes 59 and 61 used in the electrode assembly 60. In the embodiments depicted in FIG. 3, wherein the electrodes are arranged in a circular configuration and the collection insert is a circular disk, openings 62 and 72 preferably have a round, oval, ellipsoid, or "D"-shape which serves to collimate the flow (i.e., reduce or eliminate the edge effect flow) of chemical signal as it passes through the collection assembly toward the electrode assembly 60.

Figure 12:
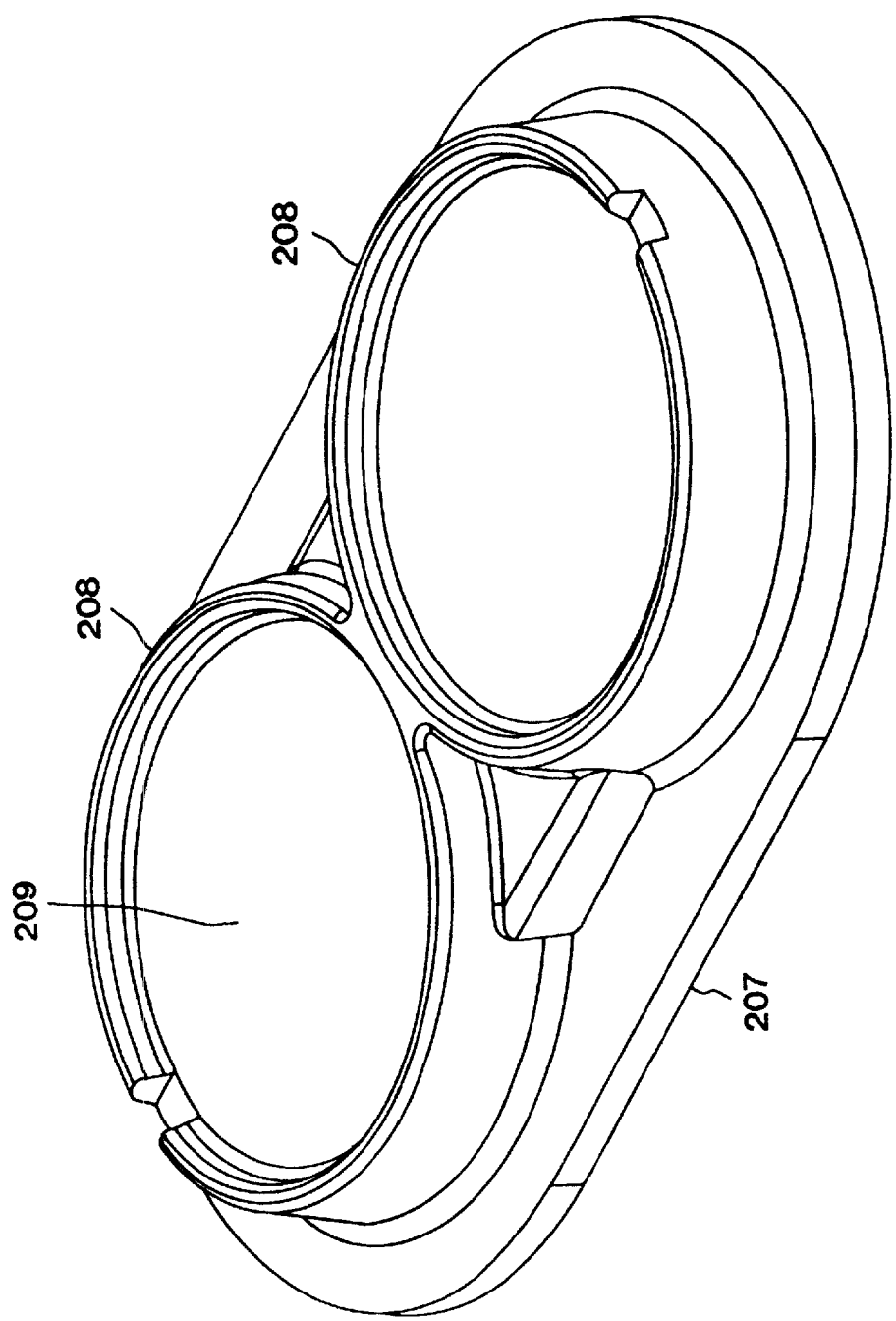
FIG. 12 illustrates one example of a contacting means for use in the press device of the present invention.

The contacting means of the press device of the present invention can be shaped and conformed to optimize the force delivered to the collection inserts when bringing them into contact with the sensor. The shape of the contacting means may, for example, be matched to the shape of the collection inserts and the electrode assembly (see, for example, FIG. 3, FIG. 12 and FIG. 13).

The openings 62 and 72 in the mask and retaining layers can be sized the same or differently, wherein the particular sizes of the openings are generally set by the overall surface area of the sensing electrode 61 that the collection assembly must operate with in the sensing device. Although the collection assemblies of the present invention can be provided in any size suitable for a targeted skin or mucosal surface, an assembly that is used with a sampling device that contacts a subject's wrist will generally have a surface area on each face in the range of about 0.5 $cm^2$ to 15 $cm^2$. The openings 62 and 72 generally expose about 50% of the area of the sensing electrode, within a manufacturing tolerance of about ±20%. In general, the openings constitute an area that is in the range of 1% to 90% of the surface area encompassed by the mask or retaining layer plus the opening(s). The openings are, however, sized smaller than the overall surface of the collection insert in at least one dimension.

The size or geometric surface area of the sensing electrode 61, the thickness of the collection insert 52, the sizes of the openings 62 and 72 in the mask and retaining layers, and the size of the overhangs provided by border regions 66 and 74 of the mask and retaining layers are all interrelated. For example, when the thickness of the collection insert is increased, the size of the opening must be decreased to obtain the same degree of reduction of edge effect flow (radial transport) of the transported chemical signal. Any decrease in the size of the openings in the mask and retaining layers increases the ability to block such unwanted flow. However, it is also desirable to maximize the size of the openings in order to maximize the amount of chemical signal which contacts the reactive surface of the sensing electrode 61.

The physical characteristics of the mask and retaining layers are selected so as to optimize the operational performance of the collection assembly. More particularly, since the assembly is intended to be contacted with a target surface for an extended period of time, the layers preferably have sufficient mechanical integrity so as to provide for such extended use. Furthermore, the layers should have sufficient flex and stretchability so as to resist tearing or rupture due to ordinary motion in the target surface, for example movement of a subjects arm when the sampling device is contacted with a forearm or wrist. The layers can also have, for example, rounded corners which tolerate a greater degree of twist and flex in a target area (without breaking contact) than layers which have sharp, angular corners. The layers also provide for some degree of sealing between the target surface and the collection assembly 50, and between the collection assembly and the electrode assembly 60, and can provide for electrical, chemical, and/or electrochemical isolation between multiple collection inserts in the collection assembly and their corresponding electrodes in the electrode assembly. Other physical characteristics include the degree of occlusivity provided by the mask layer, adhesion to the target surface and/or electrode assembly, and mechanical containment of the associated collection insert(s). In one embodiment, the collection assembly includes two collection inserts (as depicted in FIG. 3), and the mask and retaining layers have corresponding central regions, 76 and 78, respectively, which are disposed between corresponding openings in the layers and provide for a further point of attachment between the two layers. As will be appreciated by the skilled artisan upon reading the present specification, this further point of attachment provides for chemical and electrical isolation between the two collection inserts.

The mask and retaining layers are preferably composed of materials that are substantially impermeable to (1) the analyte (chemical signal) to be detected (e.g., glucose), and (2) electrolytes (ions); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode used in conjunction with the mask and retaining layers. Examples of materials that can be used to form the layers include, without limitation, polymeric materials such as polyethylene (PE) and very low density polyethylene (VLDPE), polyurethane (PU), polypropylene (PP), polyethylene terephthalate (PET), nylon, and the like; adhesive materials such as acrylate, and styrene butadiene rubber (SBR); and natural or synthetic rubbers such as latex. In this regard, each layer can be composed of a single material, or can be composed of two or more materials (e.g., multiple layers of the same or different materials) to form a chemical signal-impermeable composition.

Methods for making the mask and retaining layers include, without limitation, extrusion processes, flow and form molding techniques, die cutting, and stamping techniques, which are all practiced according to methods well known in the art. Most preferably, the layers are manufactured in a manner that is the most economical without compromising performance (e.g., impermeability to a chemical signal, the ability to manipulate the layers by hand without breaking or otherwise compromising operability, and the like). The layers may further have an adhesive coating (e.g., a pressure sensitive adhesive) on one or both surfaces. Further, the mask and retaining layers may be coated with a material which absorbs one or more compounds or ions that may be extracted into the collection insert during sampling.

Because the collection assemblies of the present invention are intended for use as consumable (replaceable) components for a sampling device, the various constituents of the assemblies are preferably manufactured and then pre-assembled in an easy-to-use laminate structure that can be inserted and then removed from the sampling device housing by the subject. In this regard, after the mask layer 58, retaining layer 68, and collection insert(s) 56 are produced, they are aligned as shown in FIG. 3, and the overhangs provided by borders 66 and 74 are attached to each other to provide a three-layer laminate which sandwiches the collection insert in between the mask and retaining layers as described above. The laminate, or a plurality of such laminates can be provided in a sealed package in order to maintain the cleanliness of the collection assembly (e.g., avoid chemical contamination from manufacturer and/or handling) prior to use, and further to avoid untoward dehydration of the collection inserts prior to use. If desired, the package can include a source of hydration (e.g., a hydrating insert formed from a water-soaked pad or gel) which ensures that the collection inserts will not dehydrate prior to use. The source of hydration is disposed of after the package laminate has been removed from the package, and thus does not form a component of the sampling device.

The pre-assembled collection assembly laminates can include one or more optional liners which facilitate handling of the assembly. For example, a removable liner 80 can be applied over the mask layer 58, particularly when the mask layer is coated with an adhesive. An additional removable liner 90 can be applied over the retaining layer 68. The removable liners 80 and 90 are intended to remain in place until just prior to use of the assembly, and are thus manufactured from any suitable material which will not be too difficult to remove, but which will remain in place during packaging, shipment and storage to provide added protection to the assembly. If the mask and/or retaining layers are coated with (or actually formed from) an adhesive, the removable liners can preferably be comprised of a polyester material which does not adhere well to commonly used contact adhesives. Other suitable materials include, without limitation, water and/or solvent impermeable polymers, metal foils, and the like.

The removable liners 80 and 90 are generally shaped to cover the outer surfaces of the mask and retaining layers. The liners can further include grasping means, such as the tab 82 depicted in FIG. 3, and intuitive indicia (such as numbering) which indicates the order in which the liners are intended to be removed during assembly of the sampling device. If desired, the liners can be shaped in a folded "V" (see, e.g., liner 90 of FIG. 3) or "Z" shape which provides a grasping means for the user, as well as providing for a controlled release motion in the liner. Alternatively, the liners can have an internal cut (e.g., a spiral cut extending from one edge of the liner and ending in the surface of the liner) or a scoring pattern which facilitates removal of the liner. Particularly, the liner material, shape, and related cuts or patterns or weakness are selected to ensure that removal of the liners does not delaminate the collection assembly, or otherwise disrupt the alignment between the various components of the collection assembly (i.e., the alignment between the mask layer, retaining layer, and the collection insert).

In one embodiment of the present invention, mechanical force is applied to the collection assembly and the electrode assembly to improve the interfacial contact between the collection inserts and the electrodes. In the assembly described in FIG. 3, removable liner 80 can be left in place and removable liner 90 is removed before application of the mechanical force. Before use of the collection/electrode assembly in a sensing device liner 80 is removed as well.

Figure 4:
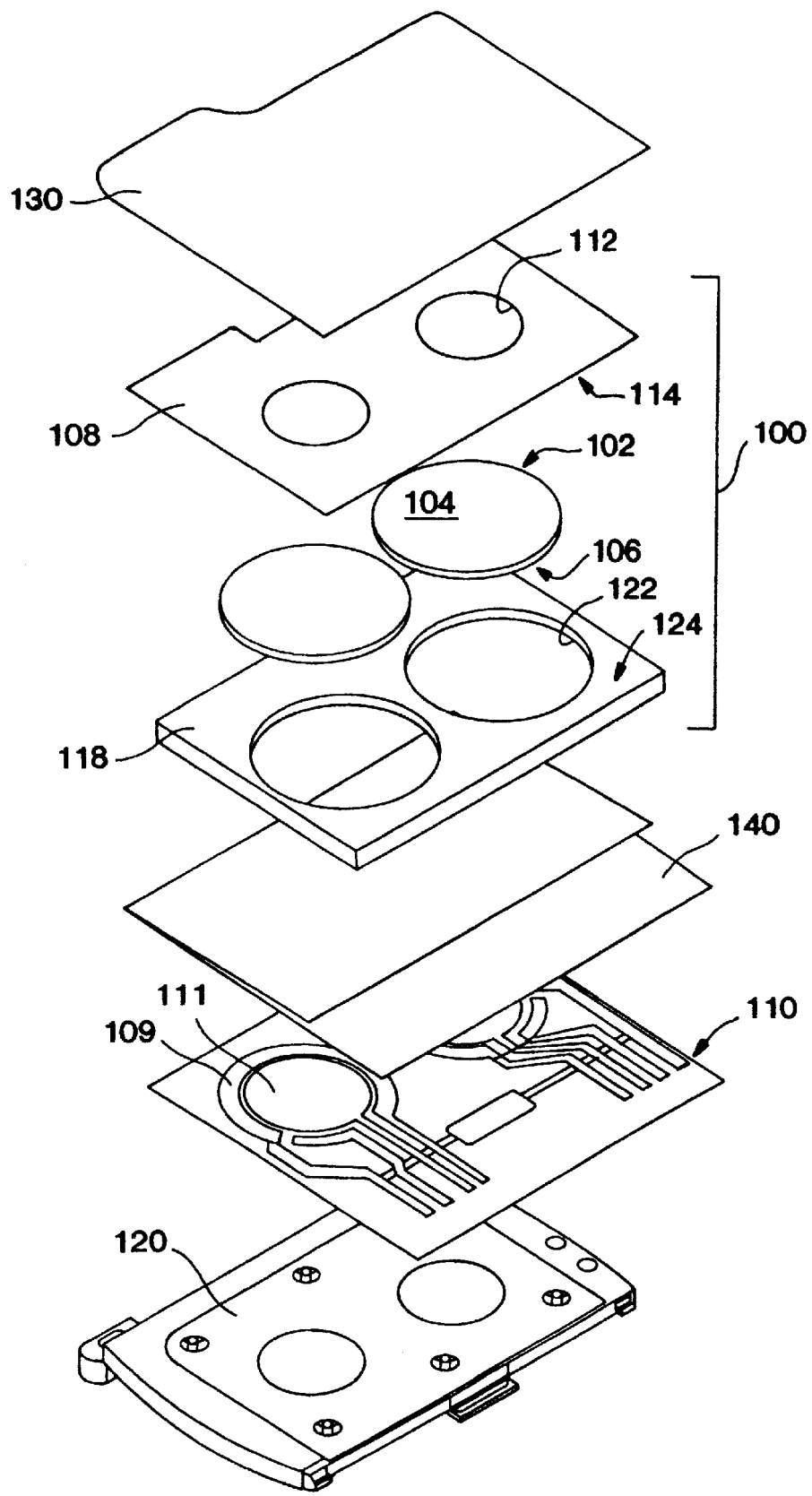
FIG. 4 depicts an exploded view of another embodiment of a collection assembly.

Referring now to FIG. 4, a related embodiment of a collection assembly produced according to the present invention is generally indicated at 100. The assembly 100 is aligned with an electrode assembly 110 which includes iontophoretic 109 and sensing electrodes 111 as described above, and is adapted to be held by a tray 120 as also described above. The collection assembly 100 includes one or more collection inserts 102 that are comprised of an ionically conductive material, and each collection insert has first and second opposing surfaces, 104 and 106, respectively.

The first opposing surface 104 of the collection insert 102 is intended for contact with a target surface (skin or mucosa), and the second opposing surface 106 is intended for contact with the electrode assembly 110, thereby establishing a flow path between the target surface and the iontophoretic and sensing electrodes. As above, a mask layer 108 is positioned over the first surface 104 of the collection insert, and includes one or more openings 112 which provide for a collimated flow path between the target surface and the electrode assembly as also described above. The opening 112 in the mask layer 108 is sized smaller in at least one dimension relative to the surface area of the collection insert 102.

A top surface 124 of a second layer 118 is positioned in facing relation with the bottom surface 114 of mask layer 108. The second layer comprises a gasket which has at least one opening 122. A two-layer laminate is formed when the mask and second layers are attached at their respective facing surfaces. The second layer also includes the collection insert 102 which is disposed within, and substantially fills the opening 122.

The physical and material properties of the mask layer are substantially identical to those of the mask layer described hereinabove, and the size and shape of the one or more openings are also determined using the above selection criteria. Furthermore, techniques for manufacture and manipulation of the mask layer 108 are substantially identical to those techniques described above. However, unlike the above-described retaining layer, the gasket in the second layer 118 of the present embodiment is intended to serve as a corral for the collection insert. More particularly, the gasket maintains the collection insert in a particular orientation such that, when the collection assembly is combined (contacted) with the electrode assembly, the collection insert is properly aligned with the iontophoretic and sensing electrodes. The gasket material further provides for electrical and/or chemical isolation between multiple collection inserts, and provides structure to the collection assembly.

The second layer gasket can be formed from any suitable material such as those materials used in the mask and retaining layers of the present invention. However, the gasket material is preferably a foam material that is sized to fit within the dimensions of the tray 120. The gasket material can further have an adhesive coating or layer which contacts the electrode assembly and provides for the facile alignment between the electrode and collection assemblies.

Optional release liners 130 and/or 140 can also be respectively applied against the mask layer 108 and second layer 118 to facilitate handling of the collection assemblies as described above. Furthermore, pre-assembled collection assembly laminates are preferably packaged, either individually or in groups, as also previously described.

Figure 5:
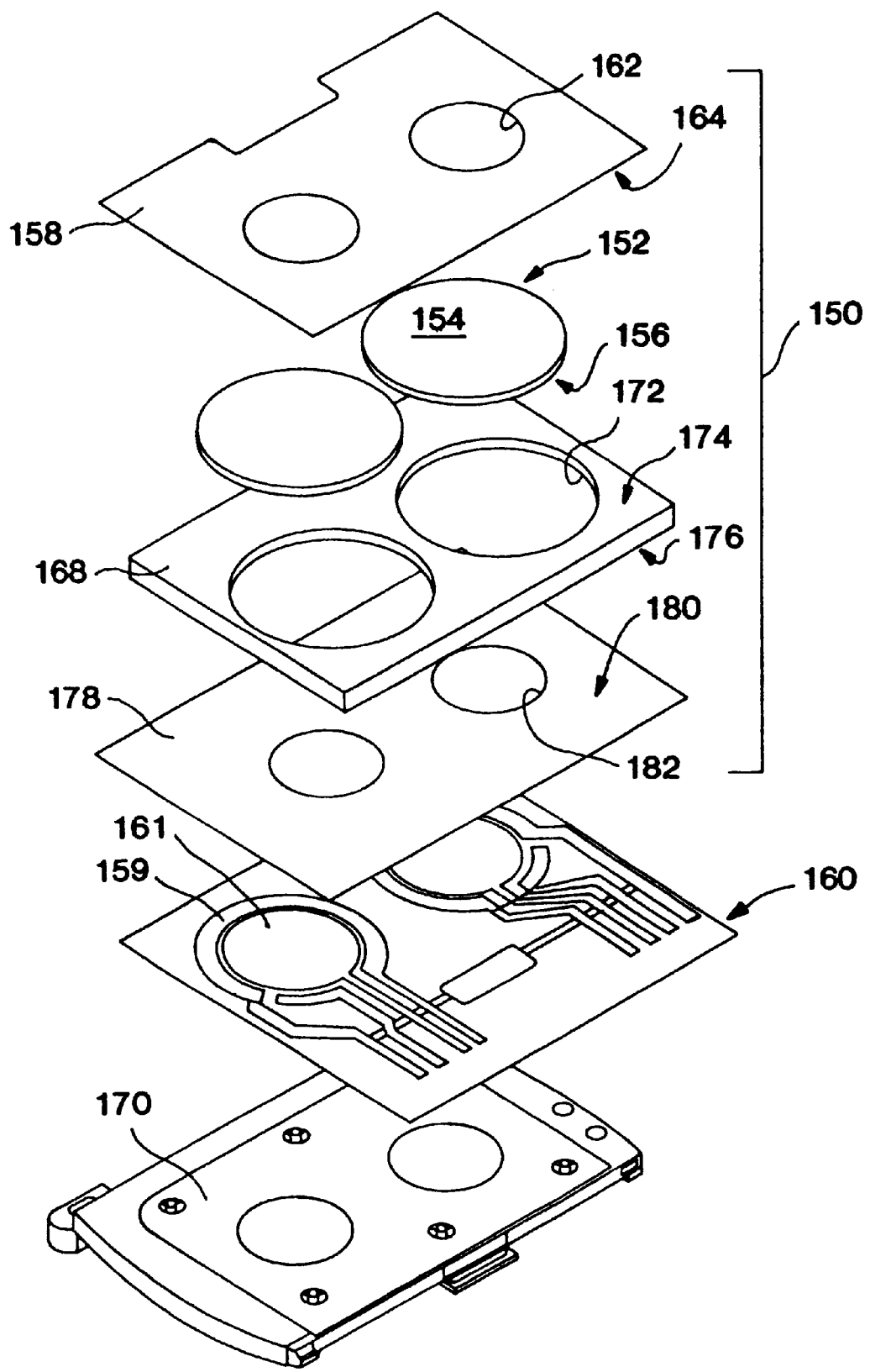
FIG. 5 depicts an exploded view of a still further embodiment of a collection assembly.

Referring now to FIG. 5, a still further related embodiment of a sampling system collection assembly is generally indicated at 150. The collection assembly 150 is aligned with an electrode assembly 160 which includes iontophoretic 159 and sensing electrodes 161 as described above, and is adapted to be held by a tray 170. The collection assembly 150 includes one or more collection inserts 152 that are comprised of an ionically conductive material, and each collection insert has first and second opposing surfaces, 154 and 156, respectively.

The first opposing surface 154 of the collection insert 152 is intended for contact with a target surface (skin or mucosa), and the second opposing surface 156 is intended for contact with the electrode assembly 160, thereby establishing a flow path between the target surface and the iontophoretic and sensing electrodes. As above, a mask layer 158 is positioned over the first surface 154 of the collection insert, and includes one or more openings 162 which provide for a collimated flow path between the target surface and the electrode assembly as also described above. The opening 162 in the mask layer 158 is sized smaller in at least one dimension relative to the surface area of the collection insert 152.

A top surface 174 of a second layer 168 is positioned in facing relation with the bottom surface 164 of the mask layer 158. The second layer comprises a gasket which has at least one opening 172. The second layer also includes the collection insert 152 which is disposed within, and substantially fills the opening 172.

The collection assembly 150 further includes a retaining layer 178, having a top surface 180 that is positioned in facing relation with the bottom surface 176 of the second layer 168. The retaining layer has at least one opening 182 which exposes at least a portion of the second surface 156 of the collection insert 152. When the corresponding surfaces of the mask layer and second layer are attached to each other, and the corresponding surfaces of the second layer and the retaining layer are attached to each other, a laminate is formed wherein both the second layer and the collection insert are sandwiched between the mask and retaining layers to provide a three-layer structure.

The physical and material properties of the mask and retaining layers are substantially identical to those of the mask and retaining layers described hereinabove, and the size and shape of the one or more openings are also determined using the above selection criteria. Furthermore, techniques for manufacture and manipulation of the mask and retaining layers 158 and 178 are substantially identical to those techniques described above. Furthermore, the physical and material properties of the second layer gasket are substantially identical to those described above.

Optional release liners can also be applied against the mask layer 158 and retaining layer 178 to facilitate handling of the collection assemblies as described above. Furthermore, pre-assembled collection assembly laminates are preferably packaged, either individually or in groups, as also previously described.

B. Exemplary Devices and Methods of the Present Invention

In one aspect, the invention includes a device that can be used to apply mechanical force to improve contact between a gel and a sensor. In a general embodiment the device includes the following elements: a first surface on which the collection assembly and the sensor assembly (for example, an electrode assembly) are placed after they are appropriately aligned; and a second surface which is conformed to contact the collection/sensor assembly in such a way as to apply an appropriate amount of mechanical force to press the collection inserts (e.g., hydrogel disks) against the sensor assembly. The amount of mechanical force used is lower than the amount of force that would cause unacceptable deformation of any components of the collection/sensor assembly, in particular, the collection inserts or the sensor. Unacceptable deformation would include, but is not limited to, the following: destroying or impairing the function of the ionically conductive gel, deforming or breaking a support tray (for a gel/sensor assembly) so that it no longer fits in the target device, deforming or breaking a gel/sensor assembly so that it no longer functions in its target device, and destroying or impairing the function of the sensor (e.g., electrode).

Typically, the first and second surfaces of the device are joined by flexible connection means (for example, a hinge). When the two surfaces are pressed together the degree of contact between the surfaces may be influenced by the addition of stopping means, i.e., means that limit how closely in contact the two surfaces can be pressed. Such stopping means provide a way to regulate the amount of pressure being applied to a gel/sensor assembly. The first and second surfaces In addition, the press device may include a latching means to hold the first and second surfaces together. Further, the latching means may be timed to release after a specified period.

Methods for making the press device of the present invention, and components thereof, include, without limitation, extrusion processes, flow and form molding techniques (e.g., injection molding), die cutting, and stamping techniques, which are all practiced according to methods well known in the art. In a preferred embodiment, the components of the device are formed by injection molding and then the device is assembled.

1. A First Embodiment of the Press Device

Figure 6:
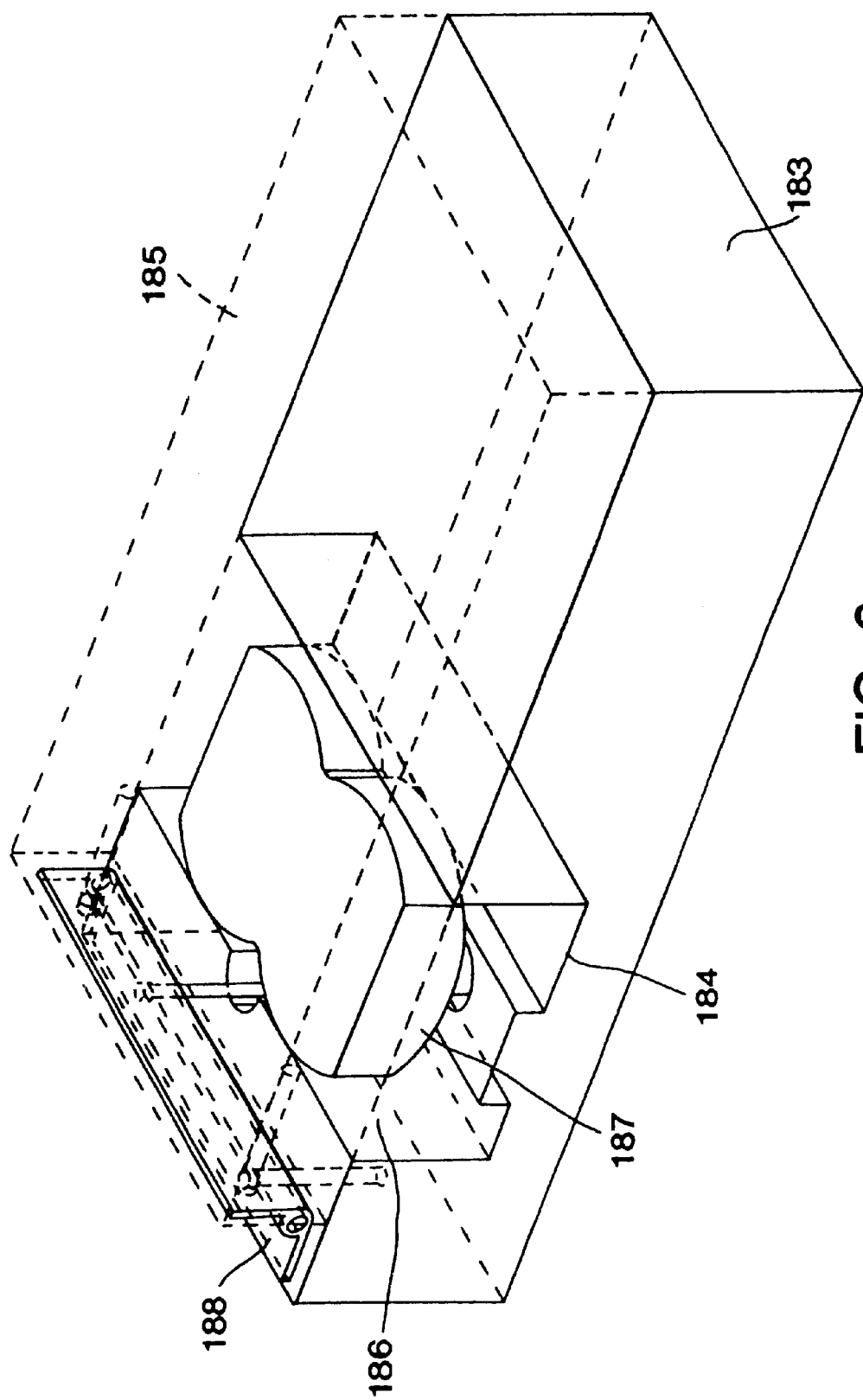
FIG. 6 presents a line drawing of one embodiment of the press device of the present invention.

One embodiment of the device of the present invention is depicted in FIG. 6. In the figure, the first surface 184 is the top surface of the press base 183, and the second surface 186 is the bottom surface of the press top 185. The first 184 and second 186 surfaces are connected by a hinge 188. The second surface has been conformed to contact the collection/sensor assembly (in such a way as to apply an appropriate amount of mechanical force to press the collection inserts (e.g., hydrogel disks) against the sensor assembly) by connecting elastomeric pads 187 (contacting means) to the second surface. An elastomeric pad can be composed of any selected elastomeric material, including but not limited to, silicone or polyurethane. The first surface 184 has been formed to hold the collection/sensor assembly in an appropriate orientation relative to the elastomeric pads 187. The thickness and surface curvature of the elastomeric pads can be empirically adjusted to provide an optimal pressure on the collection/sensor assembly that results in the desired degree of contact between the hydrogel and the sensor.

Examples of pressures (typically at room temperature) for use in the practice of the present invention include, but are not limited to, (1) 50 psi for 3–900 seconds, preferably for about 10 seconds, and (2) pressures as low as about 15 psi for about 10 seconds. Other useful pressures and times can be determined as described above.

Figure 7:
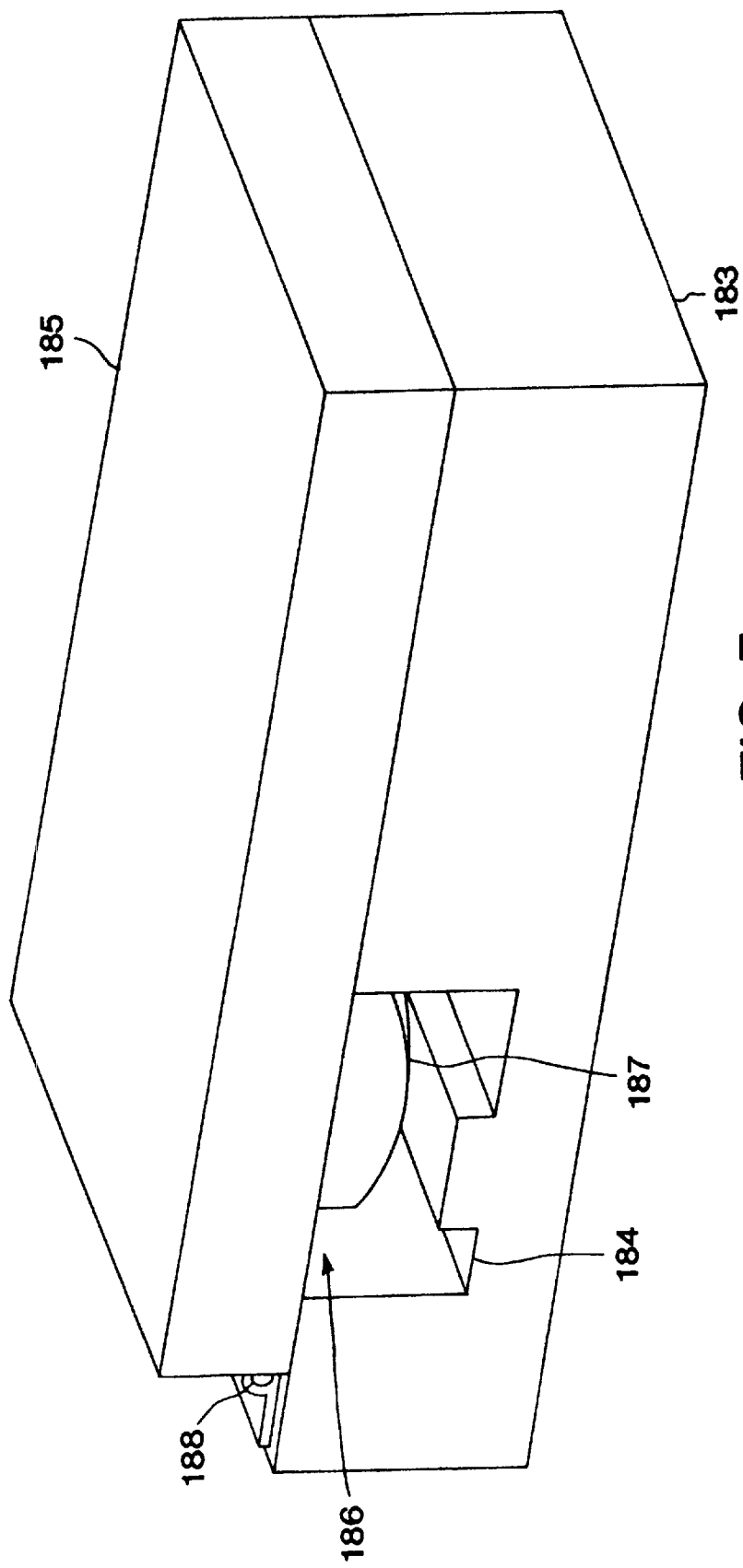
FIG. 7 shows a shaded, "solid" representation of the press device depicted in FIG. 6.

FIG. 7 depicts a "solid" version of the device shown in FIG. 6.

In this embodiment of the invention (FIGS. 6 and 7) a user lifts the press top 185 and places a collection/sensor assembly on the first surface 184 of the press device. (The plow-fold liner, for example, FIG. 4, 140, is removed to allow contact between the gel and sensor.) The press top 185 is then lowered until the elastomeric pads 187 contact the collection/sensor assembly. The user then applies mechanical force (for example, by pressing down) to the press top 185 and maintains the mechanical force for a specified period of time (typically greater than about 5 seconds and less than about 2 minutes).

Alternately, a latch means can be used to hold the two surfaces of the device in contact (for example, a hook or an interlocking mechanism). The latch means may also be timed to release after a specified period.

Further, in FIG. 6 the second surface 186 has been conformed to contact the collection/sensor assembly by addition of two elastomeric pads 187 each with a defined thickness and surface curvature. When forming the press device of the present invention, the second surface can be conformed in a variety of ways to achieve the appropriate degree of contact with the collection/sensor assembly, including, but not limited to: (1) having the conformation be intrinsic to the second surface itself (for example, a plastic injection molded press top with an appropriately conformed second surface); or (2) addition of contacting means to the second surface (for example, the elastomeric pads described above, including, but not limited to, silicone pads, or molded, flexible urethane pad(s)). Such contacting means can be formed from a variety of substances having suitable compression/pressure-generation characteristics.

2. A Second Embodiment of the Press Device

Figure 22A:
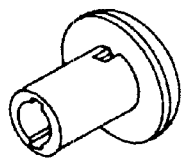
FIGS. 22A–D present illustrations of a pivot pin involved in creating hinge means to connect the top and bottom components of the press device shown in FIG. 16A.
Figure 22B:
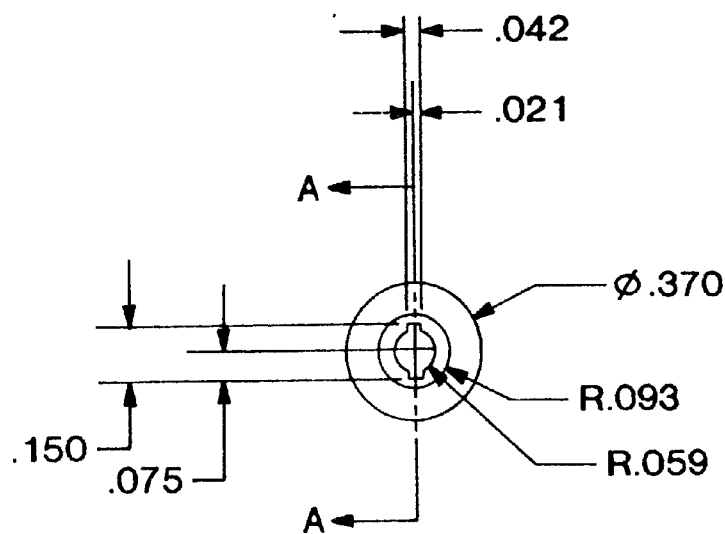
Figure 22C:
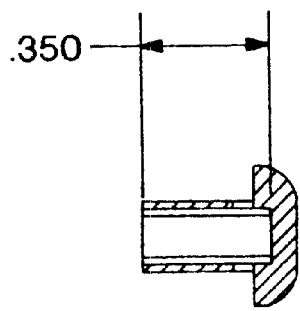
Figure 22D:
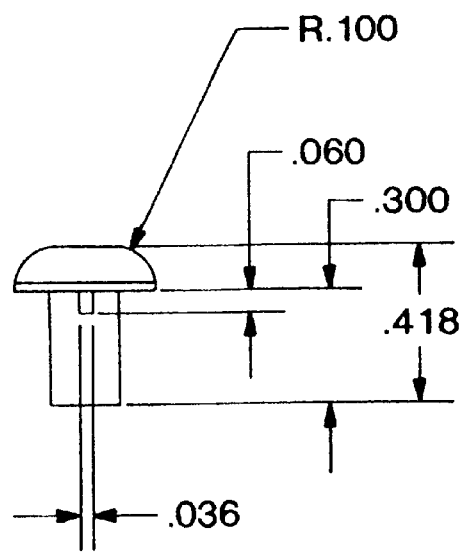
Figure 23:
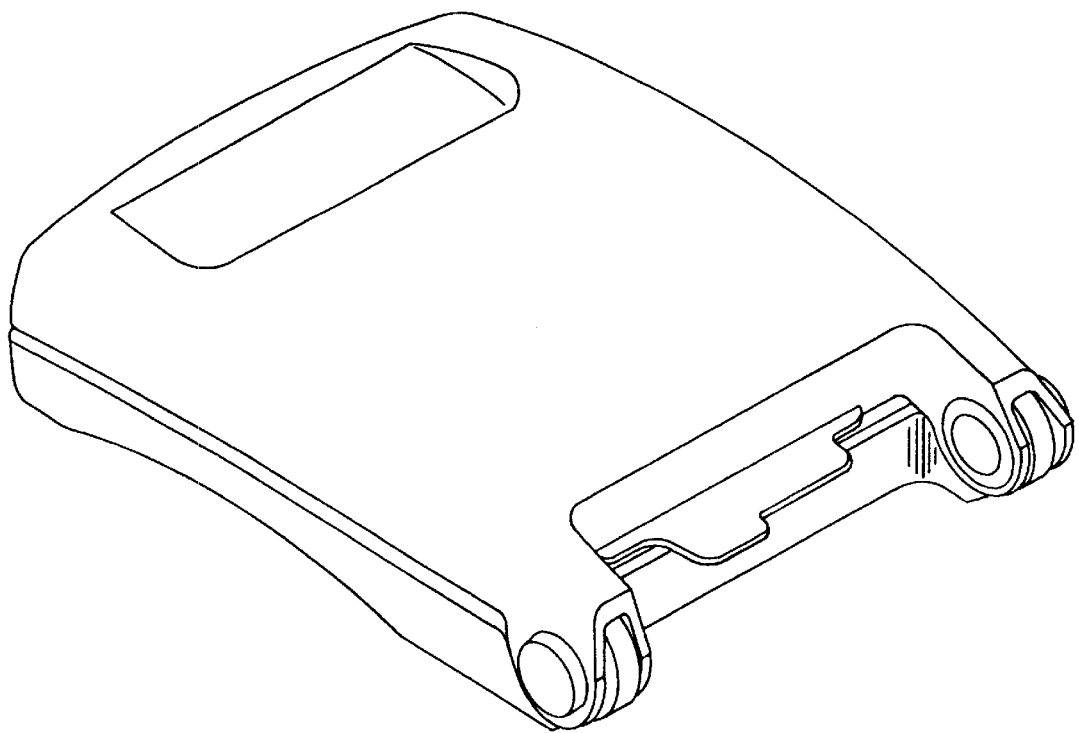
FIG. 23 presents an illustration (solid view) of the press device shown in FIG. 24 when the press device is in the closed position.
Figure 24:
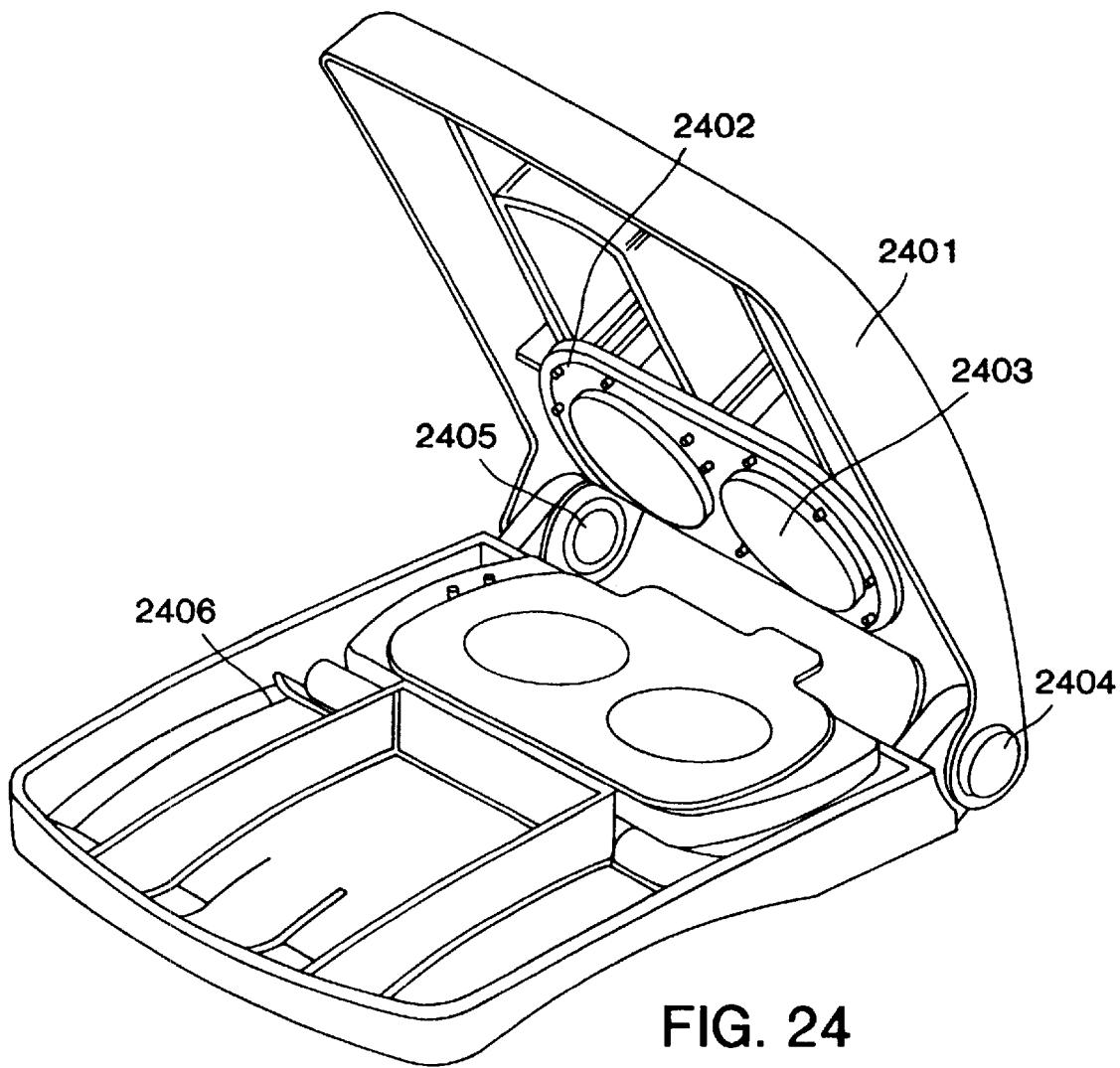
FIG. 24 presents an illustration (solid view) of the major components of one embodiment of the press device shown in FIG. 16A.

A second embodiment of the press device of the present invention is illustrated in FIGS. 16–24. The major components of this embodiment of the press device are shown in FIG. 24 including the top component of the device 2401, a pair of elastomeric domes (an example of contacting means) formed as a single piece 2403, a ring mount designed to hold the pair of elastomeric domes (formed as a single piece) 2402, the base (bottom component) of the device 2406, and connecting means (in this case hinge means) to hold the top and bottom of the device together including a pivot pin 2405 and a corresponding latch pin 2404. In FIG. 24 an autosensor (including a two hydrogels and sensor electrodes) is shown in the bottom of the device at the contact position corresponding to the pair of elastomeric domes. This is one example of functional alignment of the gels, sensors, and elastomeric material used to provide pressure to the gel/sensor.

FIG. 23 presents a view of the device when it is pressed closed. In the figure a protective liner can be seen to be protruding between the two hinging means. The liner between the gel and the sensor (e.g., plowfold liner 2708, FIG. 27) is removed before application of pressure to the gel and sensor. The patient liner, e.g., covering the top of the gel surfaces that will contact the elastomeric surfaces of the device, typically remains in place during the application of pressure. A removable liner of this type is illustrated in FIG. 27, removable liner 2716.

Figure 16A:
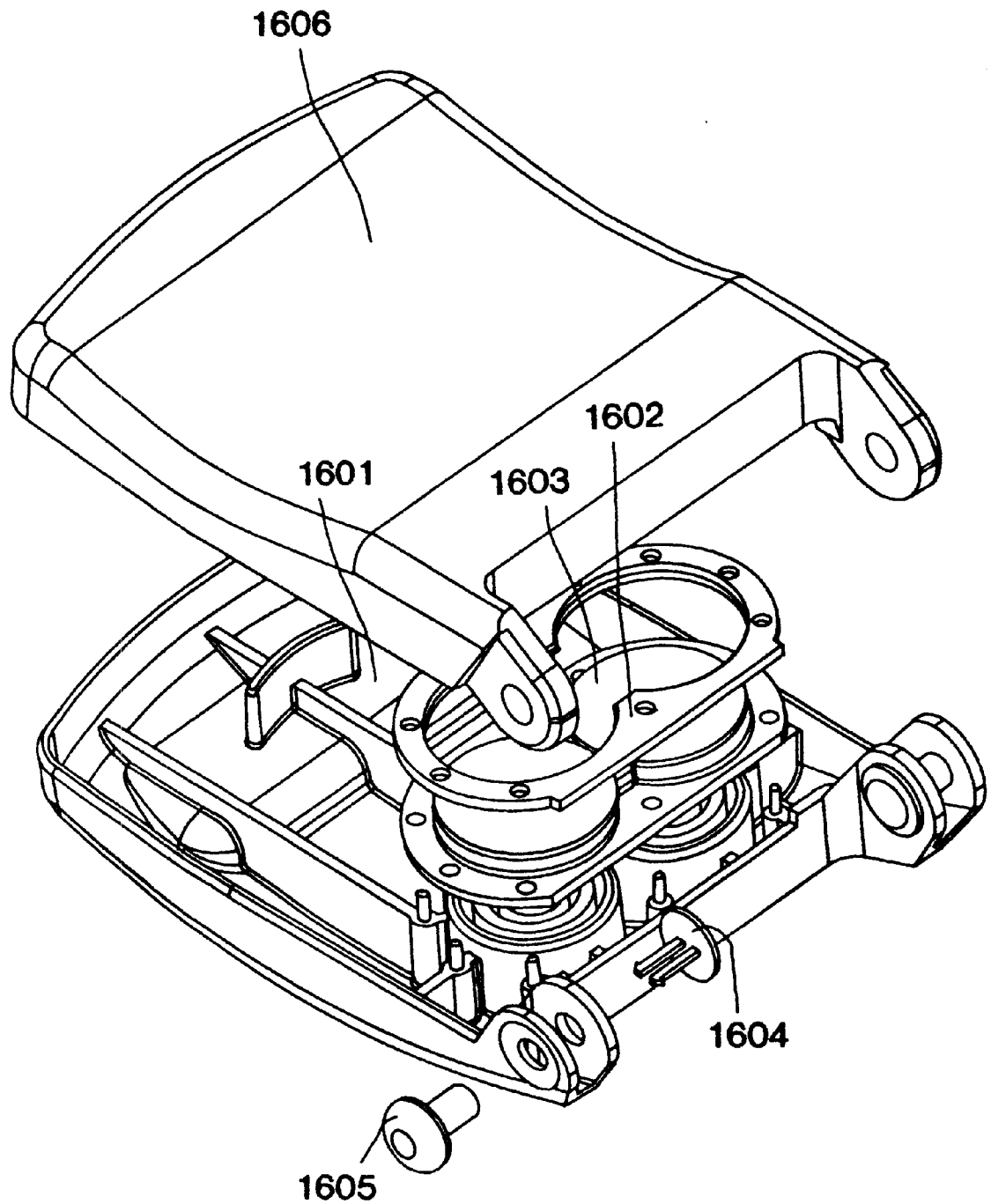
FIG. 16A presents an illustration of an exploded view of an embodiment of the press device of the present invention corresponding to the solid views of the device shown in FIGS. 23 and 24.
Figure 16B:
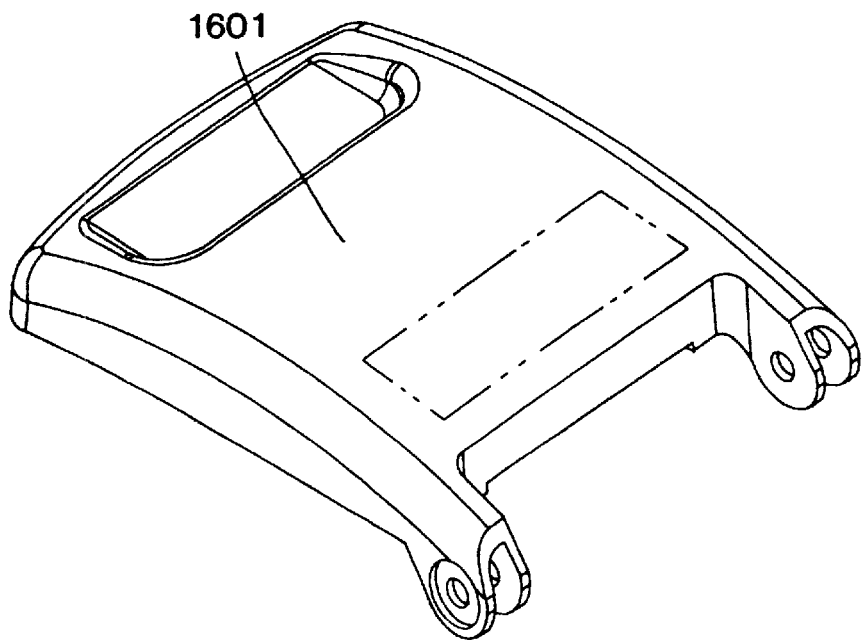
FIG. 16B presents an illustration of further detail of the top of the device.

FIG. 16A presents an illustration of an exploded view of the solid device shown in FIGS. 23 and 24. In FIG. 16A the following components are generally indicated: the top of the device 1601, a pair of elastomeric domes formed as a single piece 1603, a ring mount designed to hold the pair of elastomeric domes (formed as a single piece) 1602, the base of the device 1606, and connecting means (in this case hinge means) to hold the top and bottom of the device together including a pivot pin 1605 and a corresponding latch 1604. Also shown in FIG. 16A is the contoured shape of the bottom of the device wherein the central portion of the bottom has a concave surface which makes the device easy to hold, as well as, flat surfaces to allow the device to sit flat on a surface, such as a table, one such flat surface of the bottom of the device is near the front end (by the hinge means) and the other is near the rear end of the device. FIG. 16B presents an illustration of further detail of the top of the device. In FIG. 16B there is a recessed area near the rear end of the top to make the device easier to hold and also to provide a specific location for the application of mechanical pressure to the device (for example, by holding this area of the top of the device and the concave area of the bottom of the device and squeezing the top and bottom of the device together until they are pressed closed). The area on the top of the device toward the front end (shown as a rectangle with some dashed lines; near the hinge means) can provide, for example, an area for labeling the device with a trade name.

FIGS. 17A–F present illustrations of the shape and dimensions of the top component of the press device. In this and the following figures the small "R" indicates a radius, a struck-through circle ("φ") indicates a diameter, a letter in a small box (such as an "A" or a "B") are datums for dimensioning, and capital letters A and B associated with a partially dashed line general indicate a sectional view (for example, a cross-sectional view). A "chamfer" is typically a chamfer angle which is an angle that a beveled surface makes with one of the original surfaces. "Chamfer" is typically preceded by a length in inches (indicating the length of the surface) and an angle (relative to a first surface), e.g., 0.015×45° Chamfer.

Figure 17A:
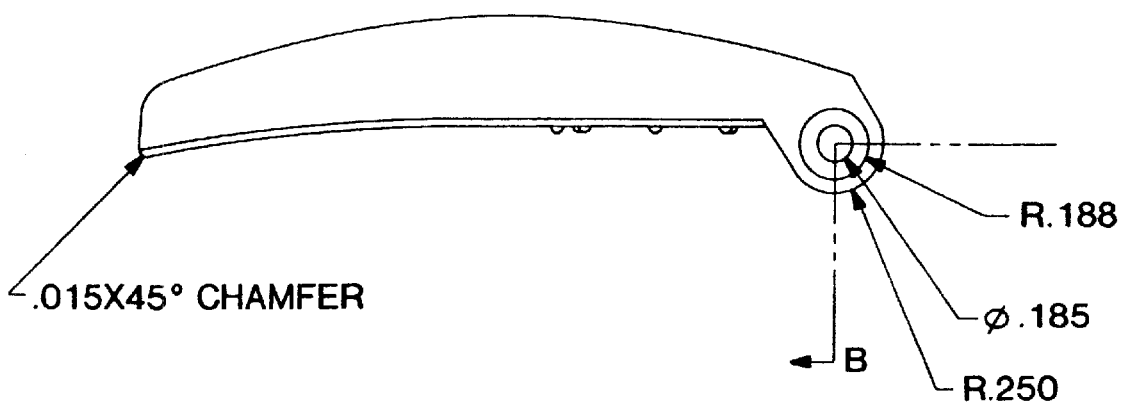
FIGS. 17A–F present illustrations of the shape and dimensions of the top component of the press device shown in FIG. 16A.
Figure 17B:
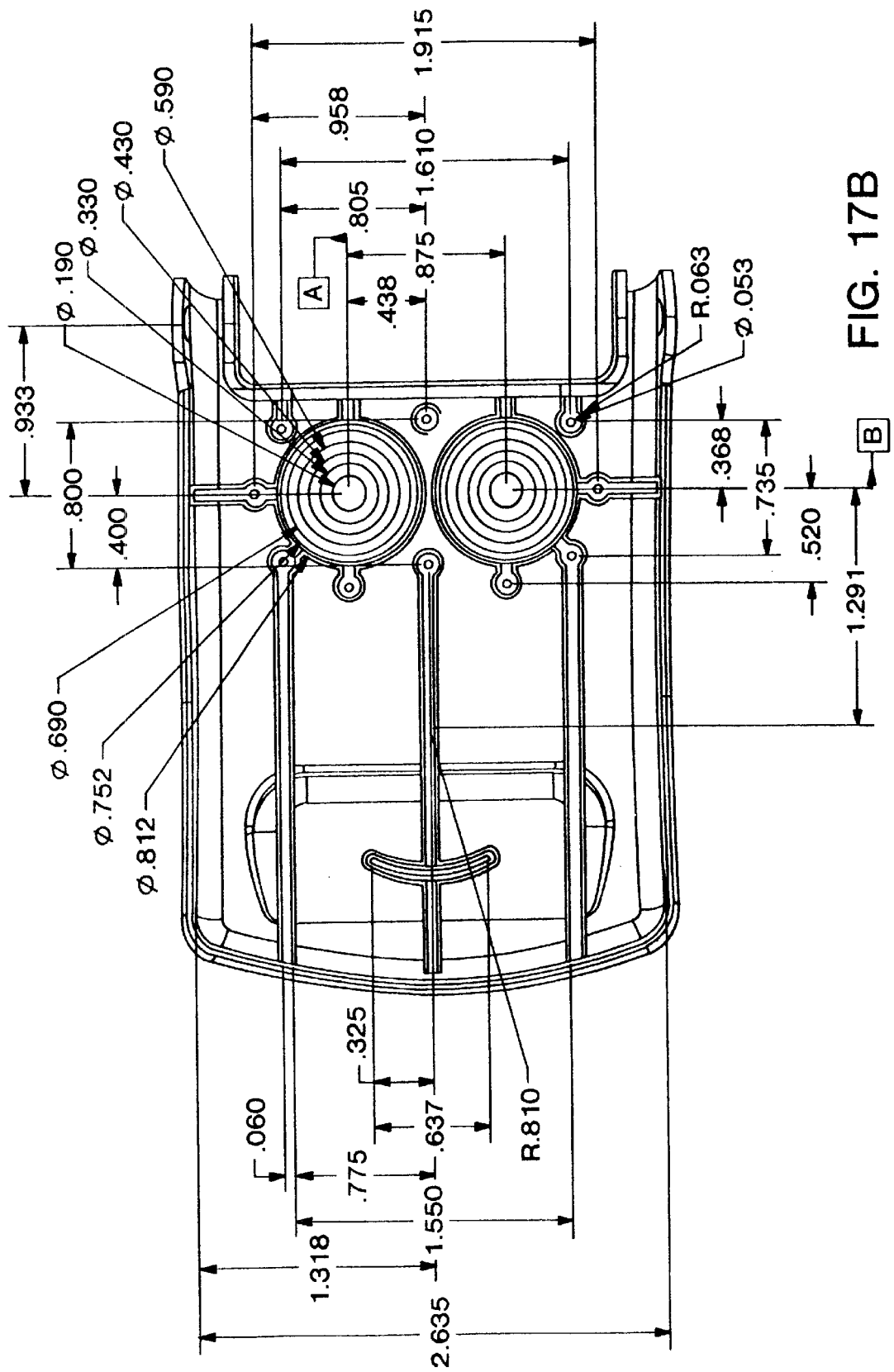
Figure 17C:
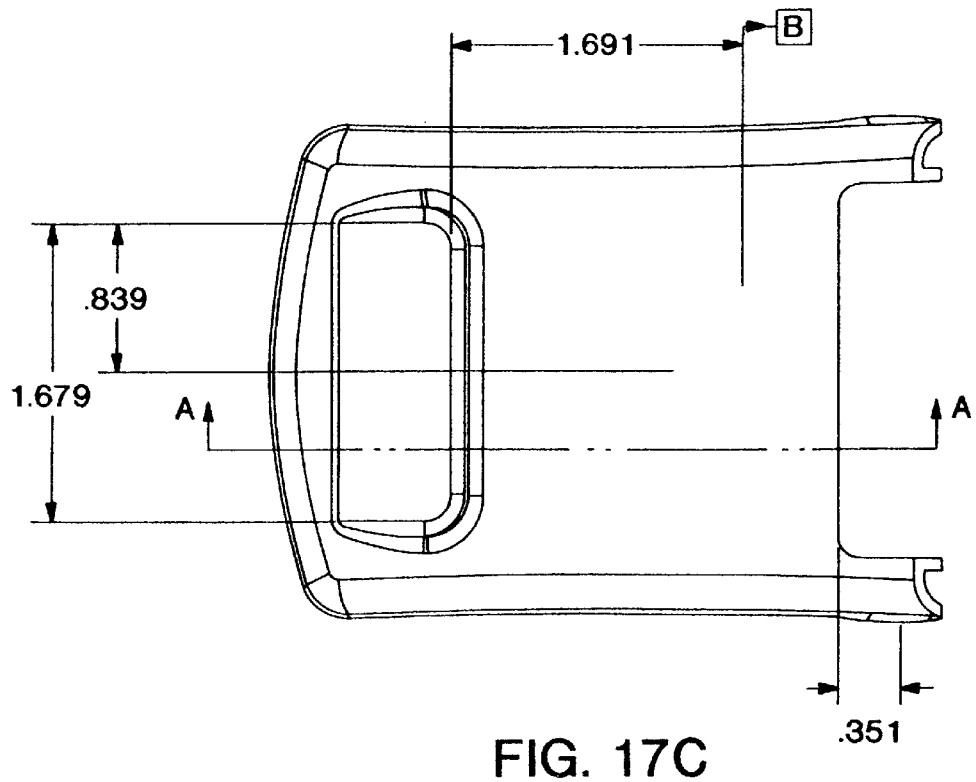
Figure 17D:
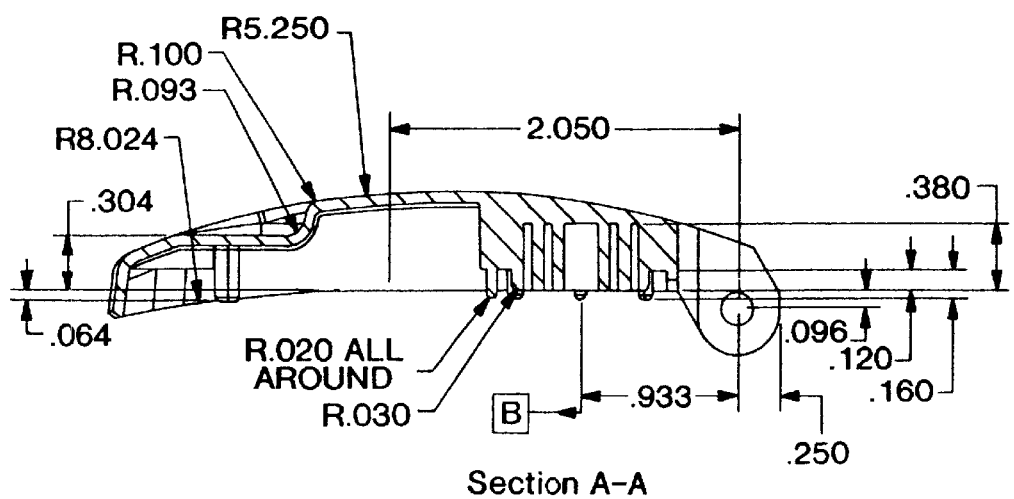
Figure 17E:
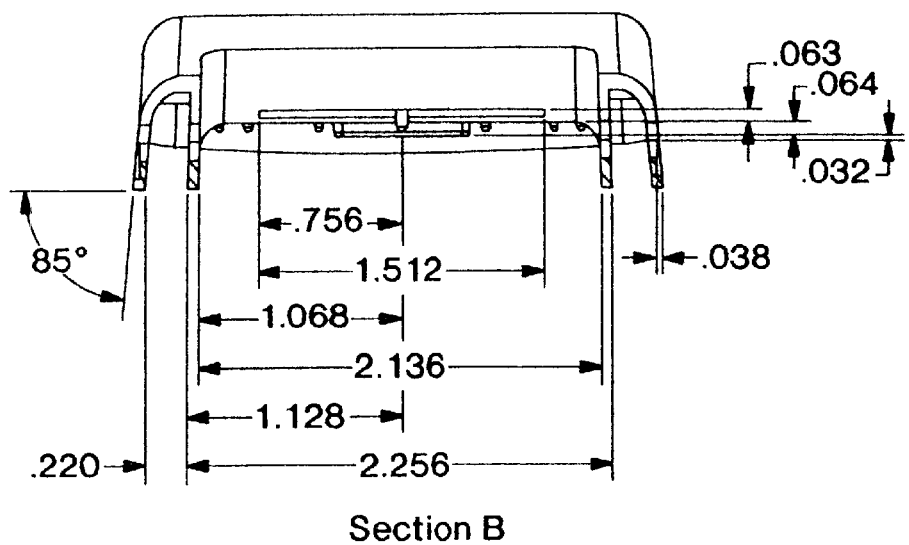
Figure 17F:
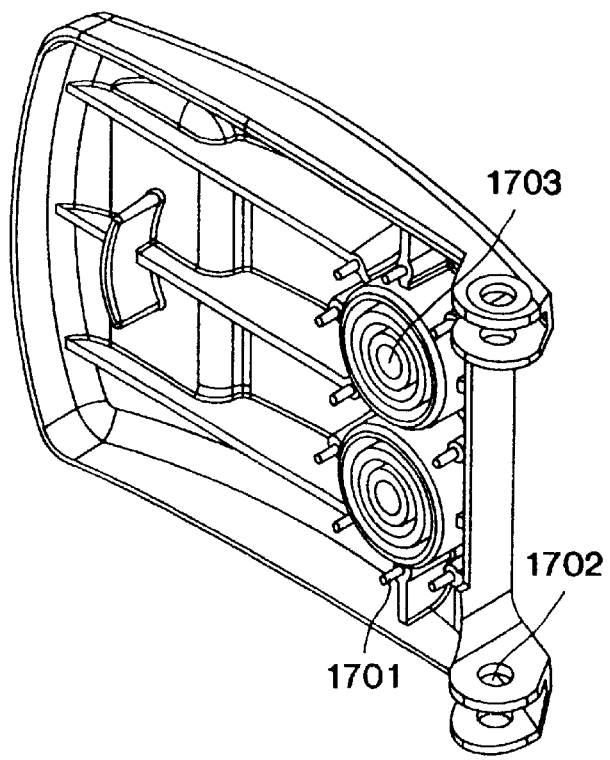

FIG. 17A presents an illustration of a side view of the top of the device, where "B" indicates the sectional area view shown in FIG. 17E. FIG. 17B presents a view of the inside of top of the device. FIG. 17C presents a view of the outside of the top of the device with cross section area A—A indicated. FIG. 17D presents a view of cross section area A—A. FIG. 17F shows a different view of the top of the device. In FIG. 17F 1701 shows the position of one of the pins used for aligning the elastomeric dome piece and then for placing a retaining ring to hold the elastomeric dome piece in place. These pins can be deformed (e.g., heat staked, creating a mushroom-type head) to lock the retaining ring in place. In FIG. 17F 1703 indicates one area where one of the elastomeric domes is seated (i.e., on the group of concentric rings shown in the figure), and 1702 indicates one of the openings used to create hinge means to connect the top and bottom components of the device.

Figure 18A:
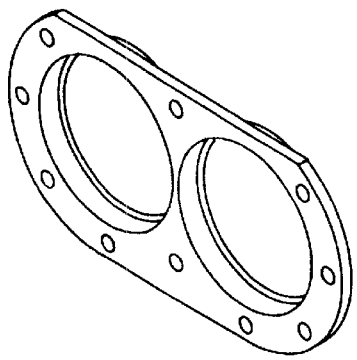
FIGS. 18A–E present illustrations of the elastomeric dome piece (an example of contacting means) of the press device shown in FIG. 16A.

FIGS. 18A–E present illustrations of the elastomeric dome piece (an example of contacting means) of this embodiment of the press device. FIG. 18A shows the single piece having a pair of elastomeric domes. This piece can be formed, for example, by liquid injection molding using silicone rubber. The final product in this case has a Durometer reading (a measure of hardness) of between about 30–35±5. Typically hardness of the material is measured with a Durometer using the "Shore A" scale (which is typically used for measuring a soft material). The Durometer reading for the elastomeric material used in the press devices of the present invention are typically in the range of between about 20 to about 60, preferably about 20–40, more preferably about 30–40, all values ±5.

Figure 18B:
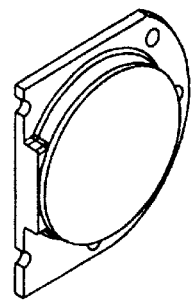

FIG. 18B shows a half-piece (i.e., a single elastomeric dome). The small circles around the perimeter of the elastomeric dome piece shown in FIGS. 18A and 18B indicate holes for placing the elastomeric dome piece over the pins illustrated, for example, in FIG. 17F, pin 1701.

Figure 18C:
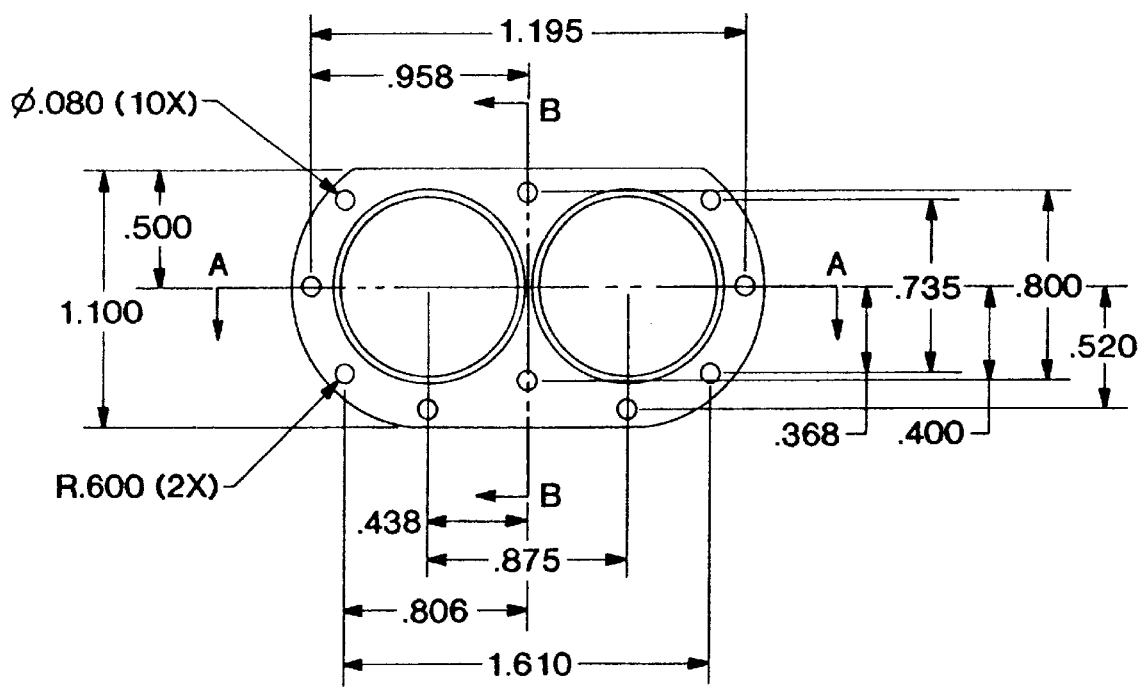
Figure 18D:
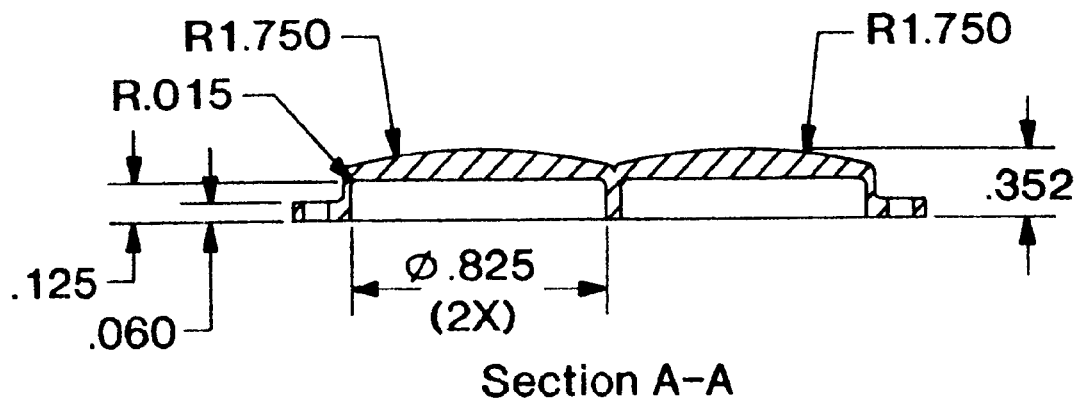
Figure 18E:
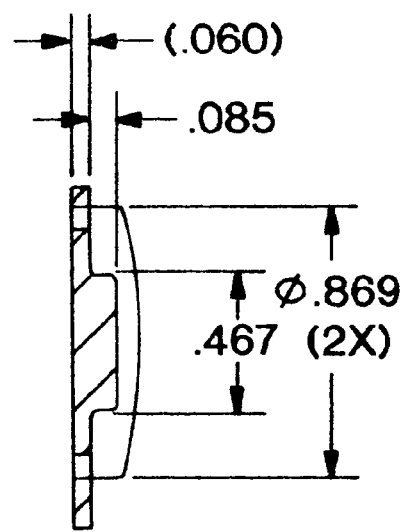

FIG. 18C shows a view of the elastomeric dome piece with associated dimensions in inches, as well as, the section lines for sections A—A (FIG. 18D) and B—B (FIG. 18E).

The shape of each elastomeric dome is typically such that when it is fully compressed (i.e., by pressing the hinged top and bottom components together to the point of contact) each compressed dome extends to the edges of the gel into which it comes in contact. In this case, the center lines of each sensor, the center lines of each gel, and the center lines of each dome are aligned.

Figure 19A:
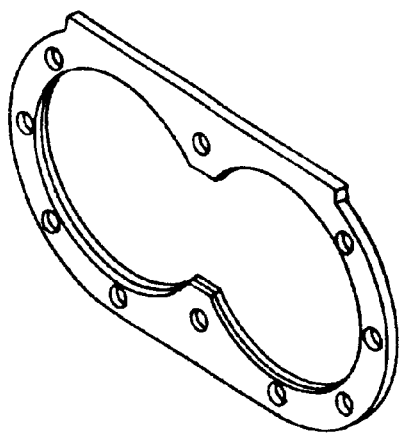
FIGS. 19A–C present illustrations of the elastomeric dome piece retaining ring of the press device shown in FIG. 16A.
Figure 19C:
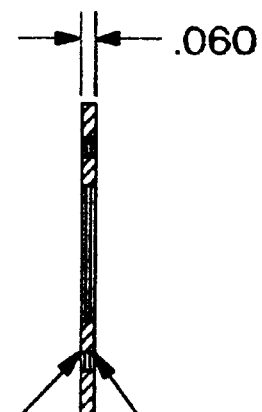
Figure 19B:
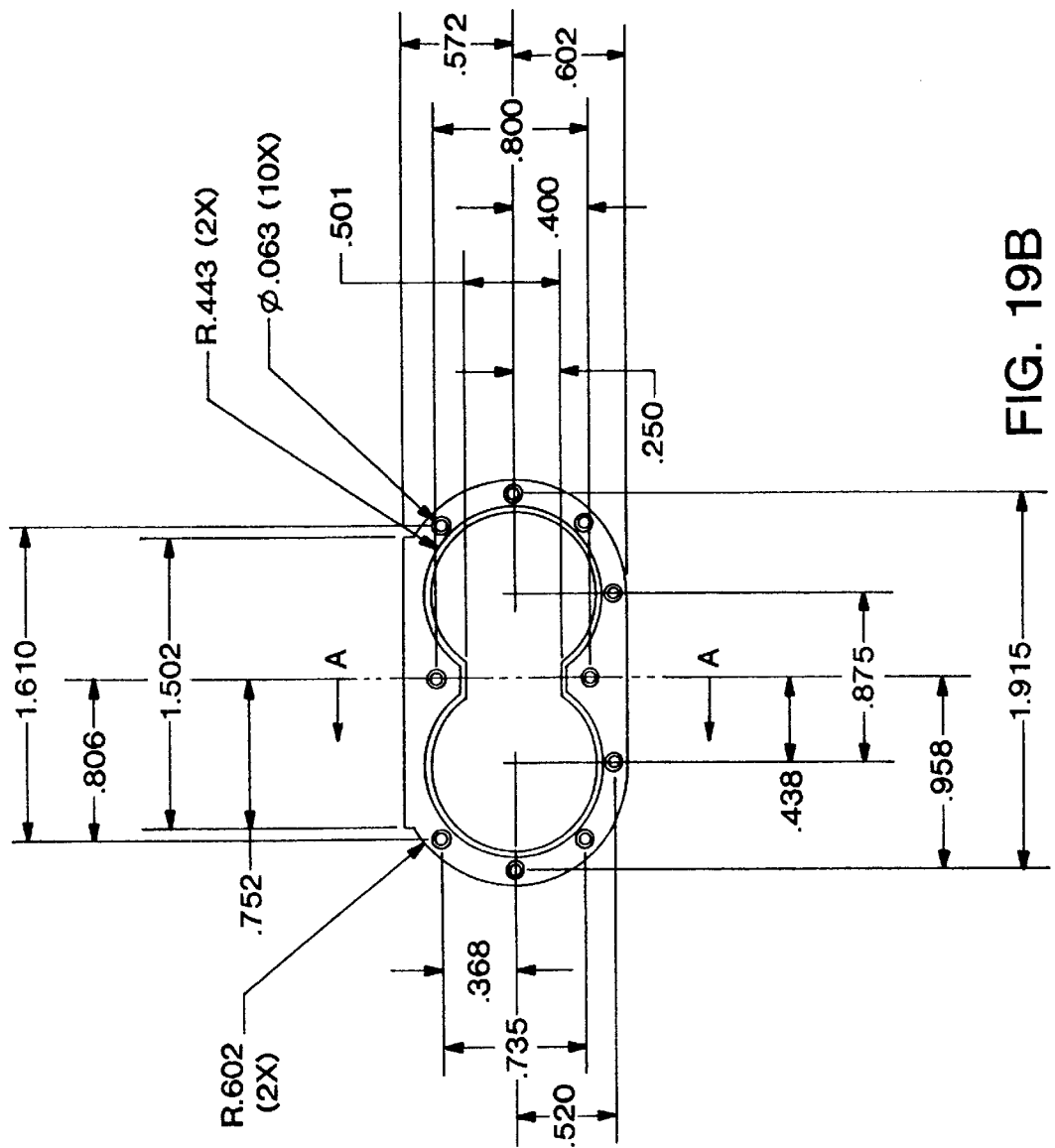

FIGS. 19A–C present illustrations of the elastomeric dome piece retaining ring. FIG. 19A shows the retaining ring. The small circles around the perimeter of the retaining ring indicate holes for placing the retaining ring over the pins illustrated, for example, in FIG. 17F, pin 1701, after the elastomeric dome piece has been put in place (e.g., see FIG. 16A). FIG. 19B shows a view of the retaining ring with associated dimensions in inches, as well as, the section lines for section A—A (FIG. 19C).

Figure 20A:
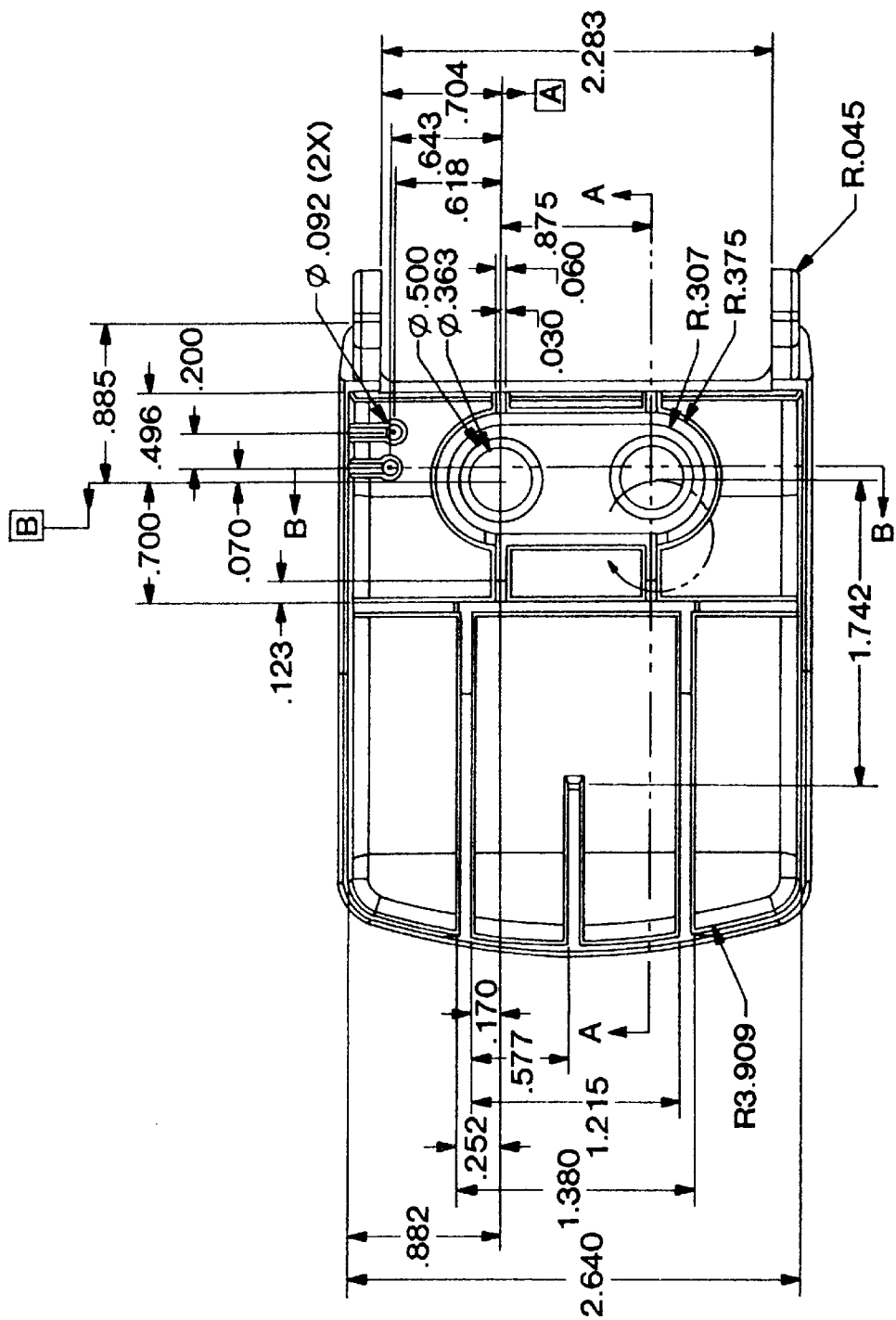
FIGS. 20A–F present illustrations of the bottom of the press device shown in FIG. 16A.
Figure 20B:
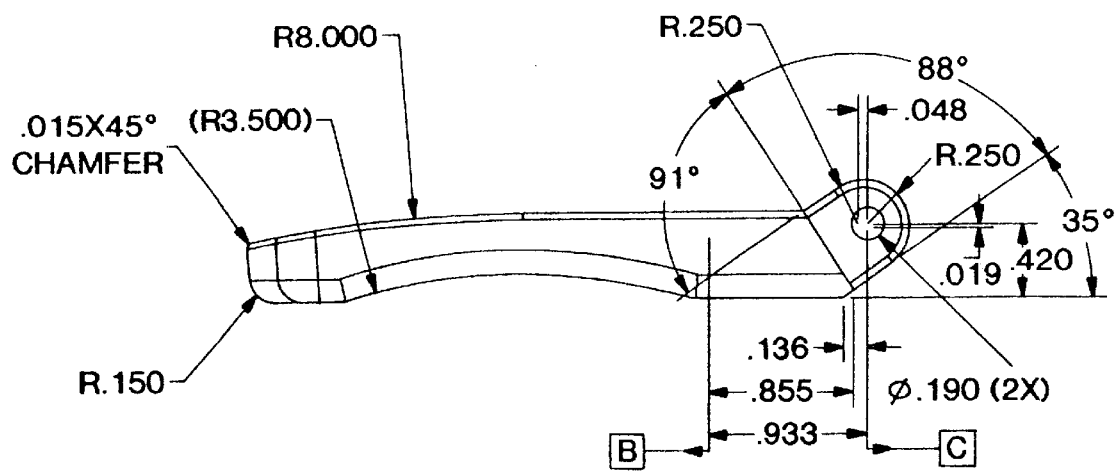
Figure 20C:
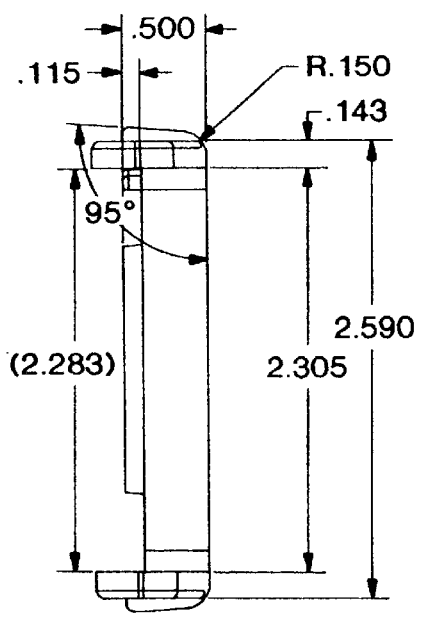
Figure 20D:
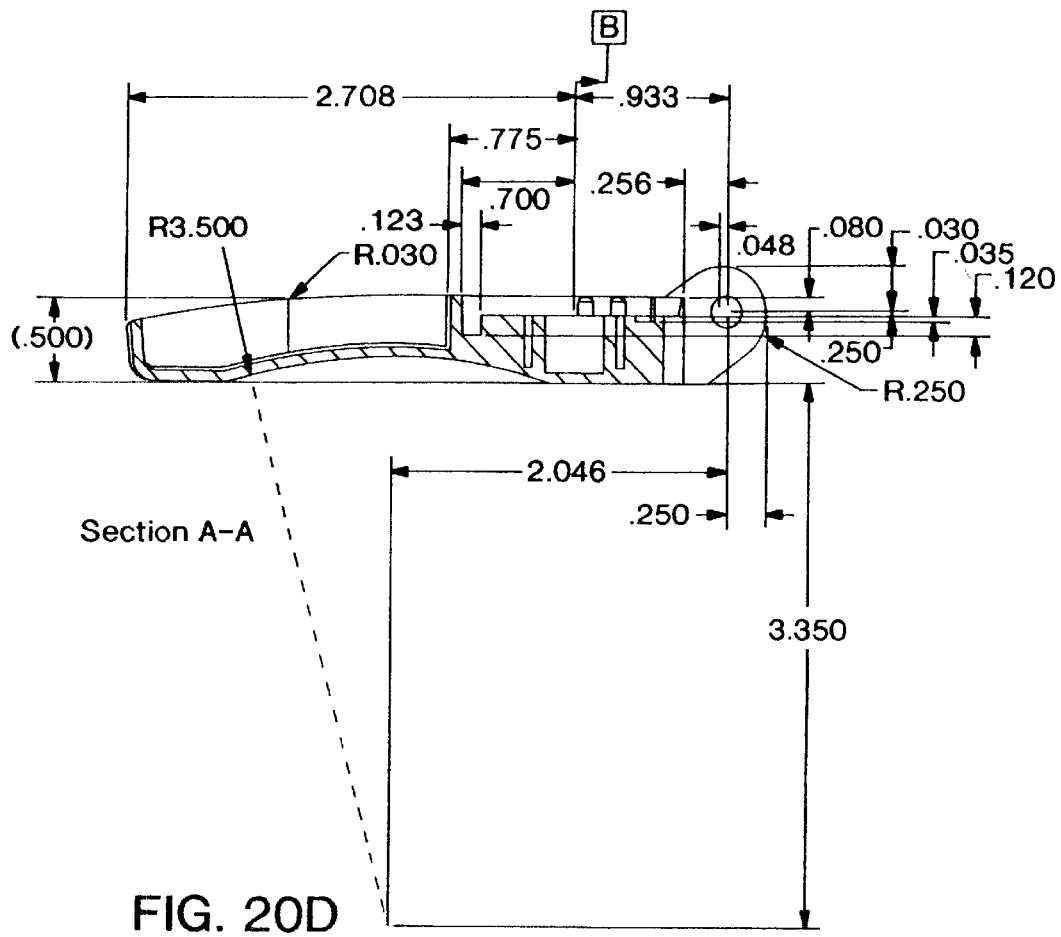
Figure 20E:
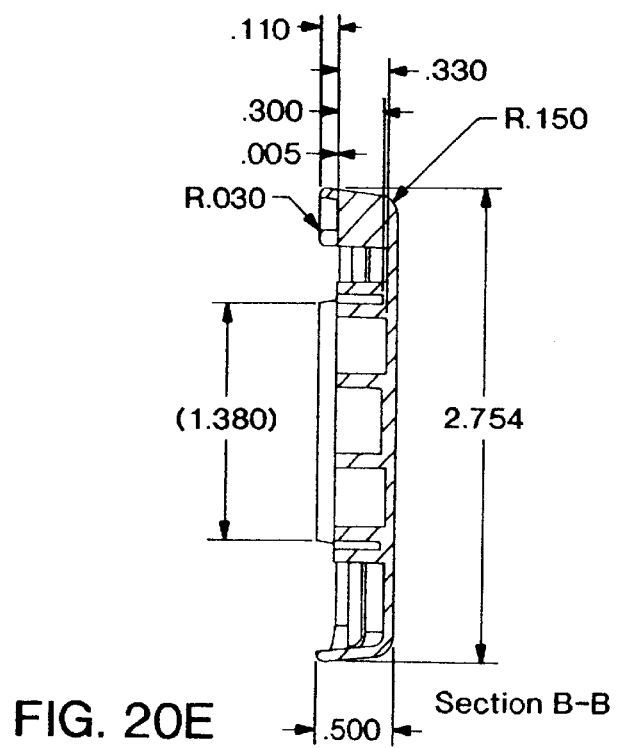
Figure 20F:
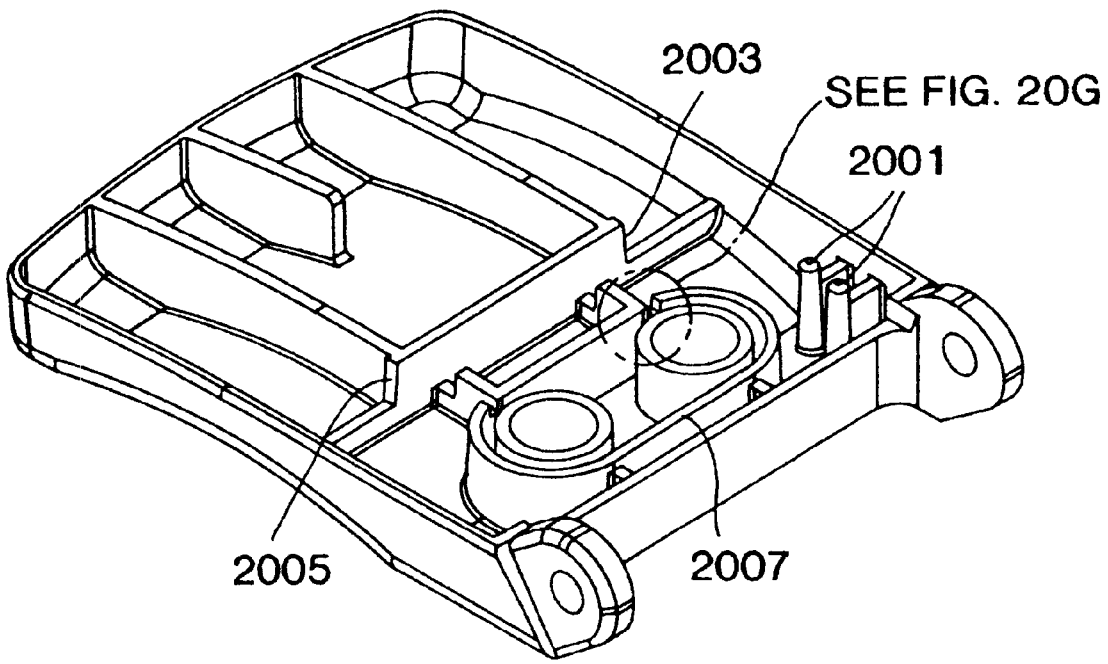
Figure 20G:
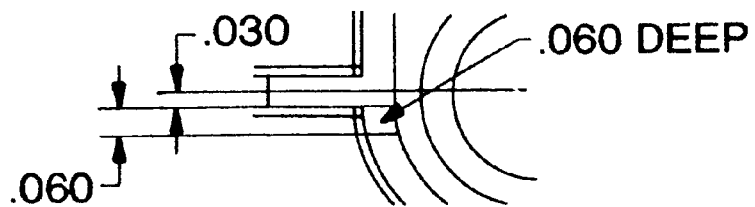

FIGS. 20A–F present illustrations of the bottom of the press device. FIG. 20A presents a view of the inside of the bottom component of the device with associated dimensions in inches as well as the lines for cross sections A—A (shown in FIG. 20D) and B—B (shown in FIG. 20E). FIG. 20B shows a side view of the bottom component of the press device. FIG. 20C shows an end view of the bottom component of the press device. FIG. 20F shows an isometric view of the bottom component of the press device, as well as, a detail of an interior configuration. In FIG. 20F two pins are shown 2001 that serve to retain a solid support for the gel and sensor in the proper orientation relative to the elastomeric domes of the elastomeric dome piece. When such pins correspond to two similar holes in the solid support (e.g., see FIG. 27, holes indicated at 2706) the pins can provide an asymmetry that insures that the solid support (e.g., 2704, FIG. 27) is placed in the press device in the proper orientation. The solid support typically rests on the area generally indicated at 2007, FIG. 20F (including the two cylindrical-like structures). The edges of the bottom component generally indicated at 2003 and 2005 serve to maintain the solid support of the gel/sensor in the proper orientation relative to the elastomeric domes of the elastomeric dome piece and to prevent unnecessary movement of the solid support when pressure is being applied to the device. Both the pins 2001 and the edges 2003 and 2005 are examples of immobilization means used to keep the gel/sensor assembly substantially immobile during the application of pressure.

FIGS. 21A–D present illustrations of a latch pin involved in creating hinge means to connect the top and bottom components of the press device. FIG. 21A shows a view of the latch pin including two prongs with ends adapted to snap into, or lock with, the pivot pin described below. FIG. 21B provides a side view of the latch pin. FIGS. 21C and 21D show drawings of the latch pin indicating dimensions. The "CL" in FIG. 21C represents the "center line."

FIGS. 22A–D present illustrations of a pivot pin involved in creating hinge means to connect the top and bottom components of the press device. FIG. 22A shows a view of the pivot pin including the lock-like structure (the open end of the pivot pin) which determines the orientation of insertion for the two prongs of the latch pin, and the openings near the cap of the pivot pin into which the ends of the latch pin are adapted to snap into and lock with. FIG. 22B shows a drawing of the pivot pin including dimensions and the line of the cross section for A—A (shown in FIG. 22C). FIGS. 22D shows a drawing of the pivot pin indicating dimensions. Use of the latch and pivot pins to create hinge means (to connect the top and bottom components of the press device) is illustrated in FIG. 16A.

All of the components described above for this embodiment of the invention (with the exception of the elastomeric dome piece) can be formed by injection molding using, for example, thermal plastics including, but not limited to, acrylonitrile butadiene-styrene (ABS; e.g., "CYCLOLAC", available from GE Plastics, Pittsfield, Mass., U.S.A.), polycarbonate, and polycarbonate/ABS blends. The elastomeric dome piece can be formed by liquid injection molding, as described above.

Although the above descriptions provide examples of specific embodiments for carrying out the present invention, they are offered for illustrative purposes only, and are not intended to limit the scope of the present invention in any way.

3. Further Embodiments of the Press Device

Figure 8:
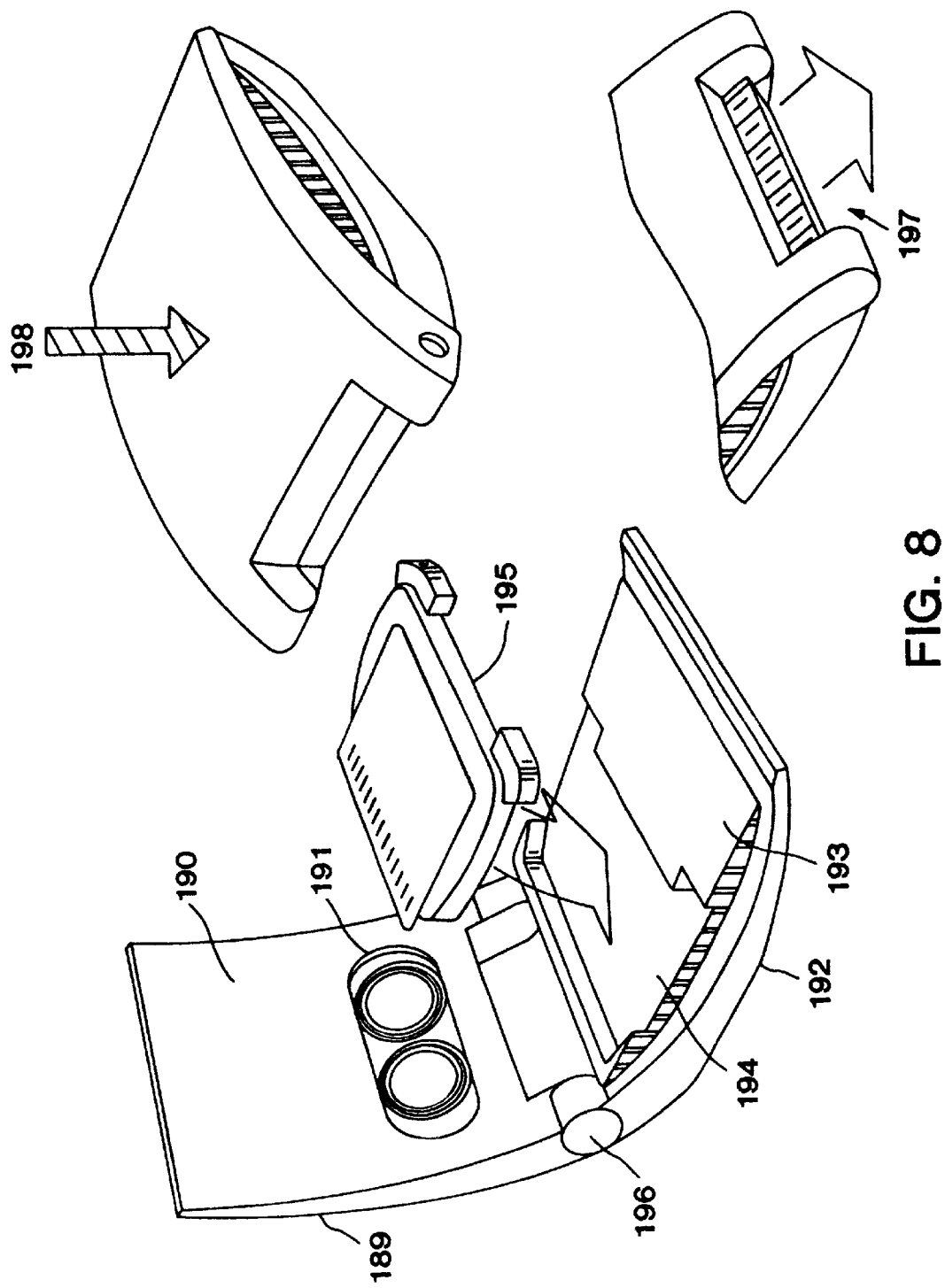
FIG. 8 depicts another embodiment of the press device of the present invention.

Further aspects and embodiments of the press device of the present invention include the following. FIG. 8 depicts a press device comprising a cover 189 with top and bottom surfaces, where the bottom surface is the above-described second surface 190. Connected to said second surface 190 are contacting means 191. The cover 189 is connected to the base 192 with top and bottom surfaces, where the top surface is the above-described first surface 193, where said first surface 193 has been adapted 194 to support a collection/sensor assembly 195. An exemplary collection/sensor assembly is depicted in FIG. 3.

The collection/sensor assembly 195 is placed in the support area 194 on the first surface 193. The cover 189 of the press device is brought into contact with the base 192, such closing is typically facilitated by a hinge means 196. The removable liner that separates the collection inserts from the electrode assembly is removed 197 (FIG. 3, removable liner 90). Further, the press device can be configured so that the liner can be removed from either end or either side of the closed press device. Alternately, the liner can be removed before placing the collection/sensor assembly into the press device. Mechanical force 198 (for example, pressure) is then applied to the cover (and/or base) of the press device for a specified period of time sufficient to provide an optimal pressure on the collection/sensor assembly which results in the desired degree of contact between the hydrogel and the sensor contained in the collection/sensor assembly.

The top cover of the press device 189 is then lifted, disengaging contact between the first 193 and second 190 surfaces. The collection/sensor assembly is then removed and is ready for use in the monitoring device.

Figure 9B:
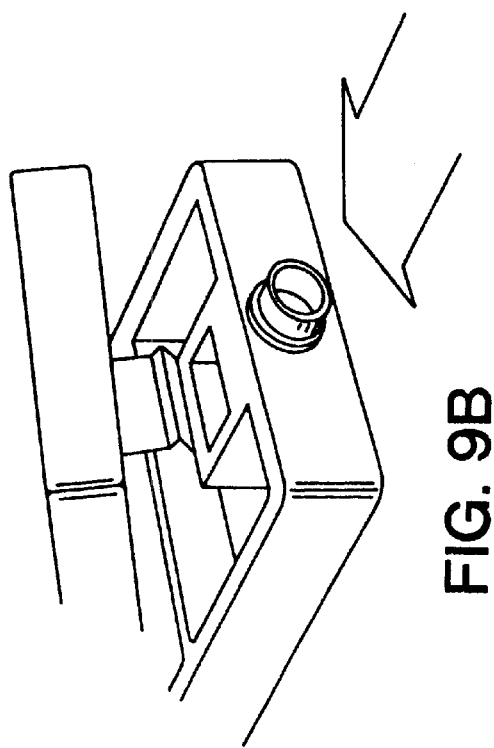
FIGS. 9A and 9B depict exemplary latching means for use in the press device of the present invention. The latching means may be used to provide the desired degree of contact between the hydrogel and the sensor contained in the collection/sensor assembly.
Figure 9C:
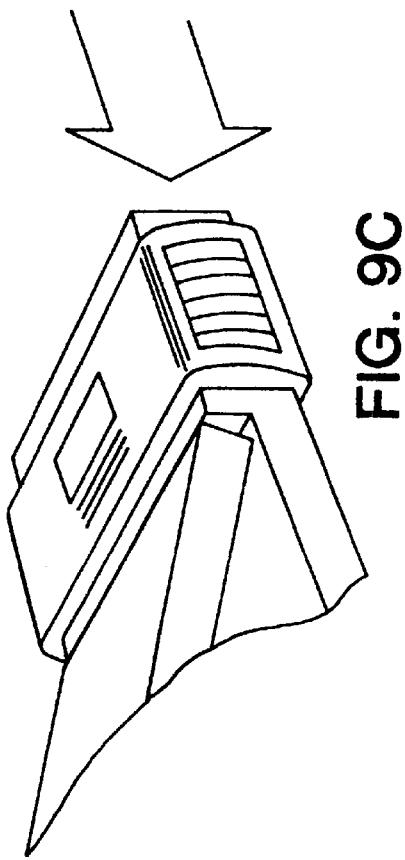
FIG. 9C depicts a sliding means for closing the press device. Such sliding means may also be used to provide the desired degree of contact between the gel and the sensor.
Figure 9A:
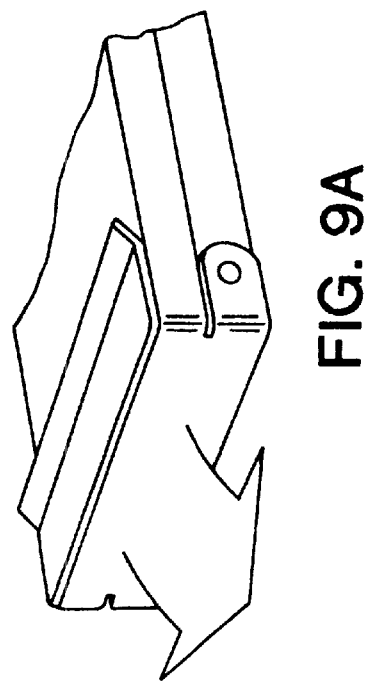

The press device can be configured, for example, with or without a latching means. Exemplary latching means are shown in FIGS. 9A, 9B and 9C. FIG. 9A depicts a metal latch attached by hinge means to either the cover or the base of a press device. When the metal latch is closed, it holds the cover and the base together and the first and second surfaces in contact. The latch means may be configured (for example, with springs or metal of appropriate flexibility) to provide the desired mechanical force to give the desired degree of contact between the hydrogel and the sensor contained in the collection/sensor assembly. Alternately, the latch means may hold the cover and base together so that an appropriate mechanical force can be applied. In FIG. 9A the arrow indicates how the metal latch may be flipped down to release.

Similarly, FIG. 9B depicts a push button release latching means. In FIG. 9B the arrow indicates a button that can be pushed to release the latching means. FIG. 9C a "slide sleeve" latching means, where a sleeve is provided that slides over the press device to hold (i.e., latch) the cover and base together.

Figure 10B:
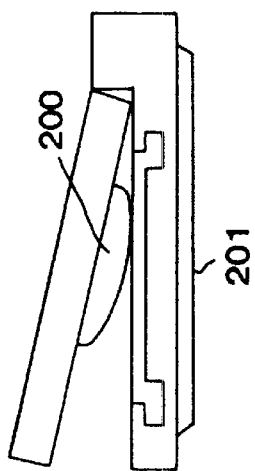
FIGS. 10A, 10B, and 10C depict an exemplary press device that encases the collection/sensor assembly and uses sliding means to deliver the desired mechanical force to provide the desired degree of contact between the hydrogel and the sensor.
Figure 10C:
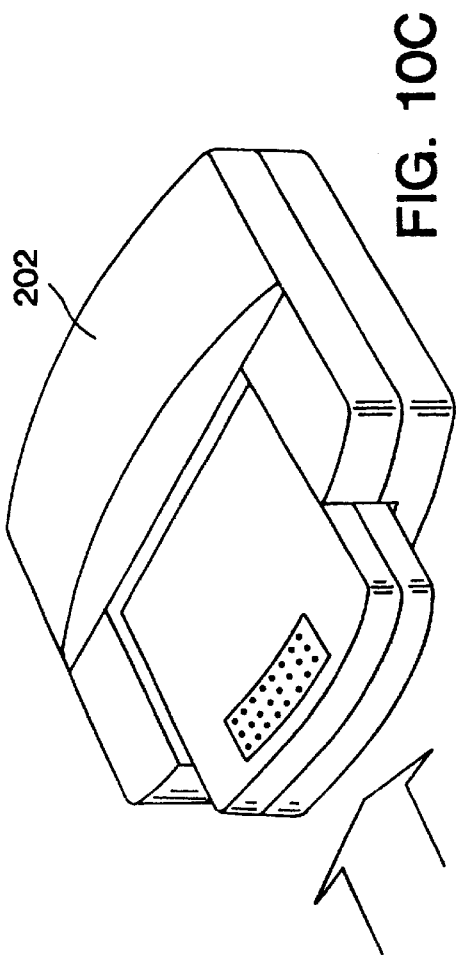
Figure 10A:
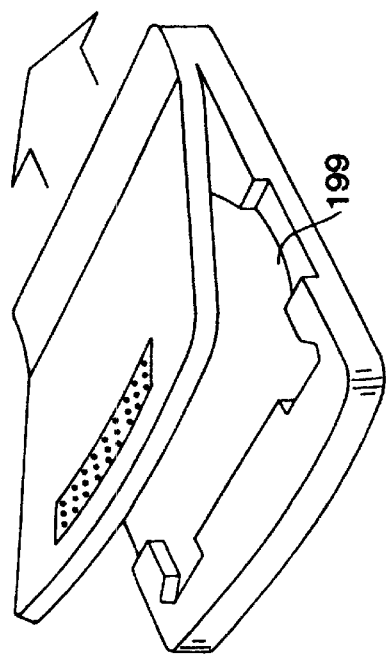

Another exemplary embodiment of the press device of the present invention is depicted in FIGS. 10A, 10B, and 10C. In this embodiment a tray carriage 199 is provided which supports the collection/sensor assembly (FIG. 10A). The tray carriage is shown in cross-section in FIG. 10B where the contacting means 200 and slide rails 201 are indicated. A collection/sensor assembly is inserted into the tray carriage, and the tray carriage is then slid into a "base unit" 202 (FIG. 10C). By sliding the tray carriage into the base unit the desired mechanical force is provided to give the desired degree of contact between the hydrogel and the sensor contained in the collection/sensor assembly. In FIG. 10C the arrow indicates the direction of sliding. Alternately, after sliding the tray carriage into the base unit an appropriate mechanical force can be applied.

Figure 11:
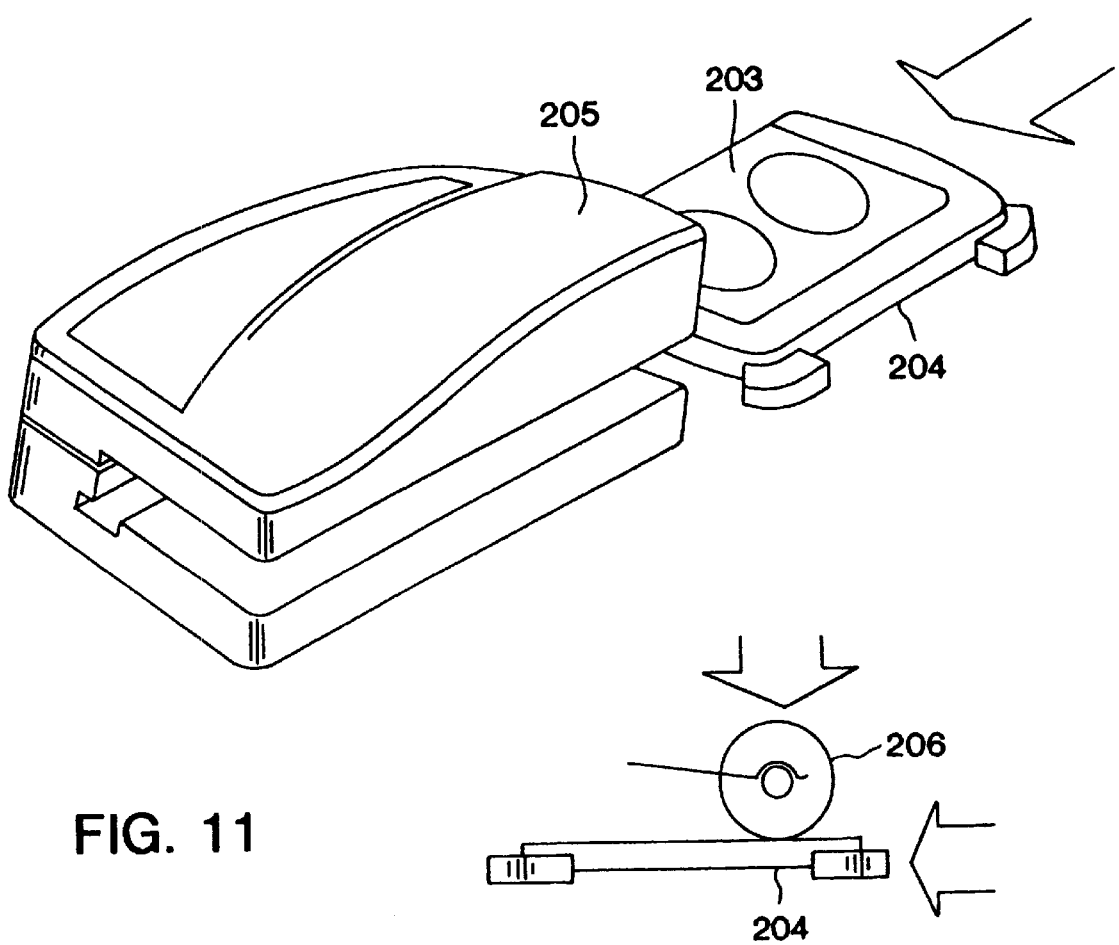
FIG. 11 depicts an exemplary press device that uses roller means to deliver the desired mechanical force to provide the desired degree of contact between the hydrogel and the sensor contained in the collection/sensor assembly.

Yet another embodiment of the press device of the present invention is depicted in FIG. 11. In this embodiment, the collection/sensor assembly 203 (for example, as shown in FIG. 3) is placed in a tray carriage 204. The tray carriage is then pressed or drawn through a "base unit" 205 containing roller means 206 capable of delivering the desired mechanical force needed to provide the desired degree of contact between the hydrogel and the sensor contained in the collection/sensor assembly. The mechanical force is applied as the tray carriage 204 is contacted with the roller means 206. The amount of mechanical force can be regulated by tension means (for example, metal bars or springs).

In the press device of the present invention, the contacting means can be formed in a number of conformations and be made from a variety of materials, such that the contacting means have suitable characteristics for delivering the desired mechanical force needed to provide the desired degree of contact between the hydrogel and the sensor. In one aspect of the present invention the contacting means is of the shape shown in FIG. 12, having a support base 207, two reservoirs with raised edges 208, and a suitable material filling each reservoir 209 to provide the desired mechanical force. The raised edges provide means for capturing the collection inserts (for example, hydrogel disks), that is, holding the collection inserts in a defined relationship to the contacting means and the sensor (see FIG. 13). The entire contacting means may be formed from a single substance, for example, silicone or urethane. Alternately, the support base and, reservoirs may be of a material having flexibility properties (for example, a more rigid material) that differ from the material within the reservoir. In another embodiment, components 208 and 209 may be formed from the same material, for example, silicone, and the base 207 of the contacting means may be of a material having different flexibility properties (for example, a more rigid material).

Figure 13:
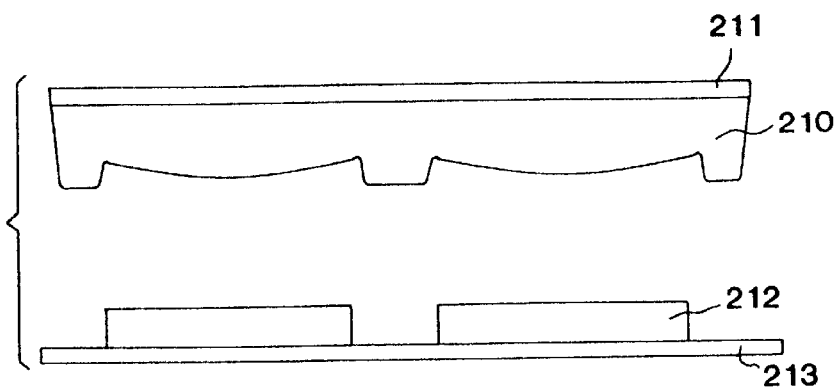
FIG. 13 depicts an example of a contacting means formed as a single pad, where the contacting means further includes a backing plate. Further, the figure shows (in cross-section) the relationship between the contacting means, the collection inserts, and the sensor.
Figure 14:
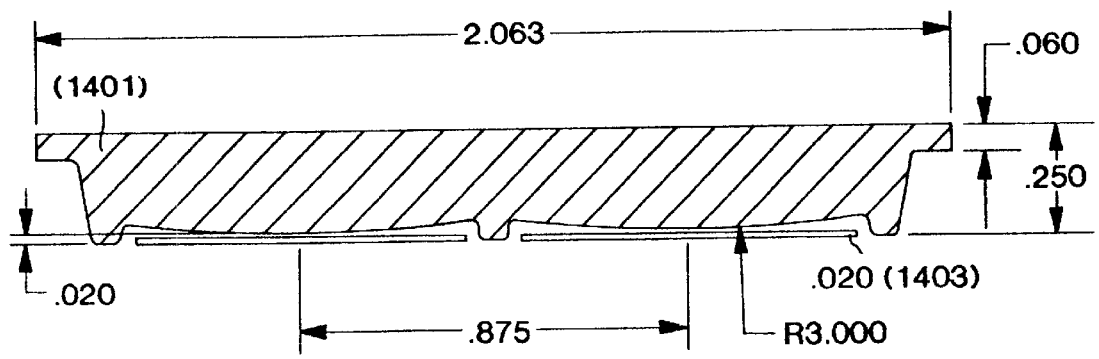
FIG. 14 provides exemplary measurements of a silicone pad contacting means in relation to two hydrogel collection disks of up to, but not limited to, about 0.020 inches in thickness.

FIG. 13 depicts an example of a contacting means formed as a single pad 210 from, for example, silicone, where the contacting means further includes a backing plate 211. FIG. 13 also demonstrates, in cross-section, the relationship between the contacting means 210, the collection inserts 212, and the sensor 213. FIG. 13 presents an example of a silicone pad to gel profile. FIG. 14 provides exemplary measurements of a silicone pad (1401) (e.g., Durometer, Shore A scale, reading of 40) contacting means in relation to two hydrogel collection disks of up to, but not limited to, about 0.020 inches thick (1403).

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

The non-invasive glucose monitoring (sampling) device described herein was used to demonstrate the efficacy of improving the contact of the hydrogel and the sensor by applying pressure to the hydrogel when bringing it into contact with the sensor. The sampling device was tested under two conditions: (1) where the hydrogel was applied to the surface of the sensor without the use of pressure; and (2) where the hydrogel was applied to the surface of the sensor followed by the application of pressure.

A known amount of glucose was injected onto the gel/sensor system, and the rate of glucose "recovery" was measured. The recovery is indicated by the electrochemical signal resulting from the reaction of the glucose with the enzyme in the gel. Two points of interest in this test were the rate of recovery, and whether 100% of the theoretical value of the recovery was achieved.

In this test, the pressure treated gel/sensor was shown to greatly increase the functional recovery of glucose. (Functional recovery is a measure of the sensitivity of the sampling device.) The percent recovery for the pressure treated gel/sensor system showed much faster response, and better overall recovery of glucose. When the sensor signal was integrated over a 7 minute interval the overall measured signal between these two systems were ~70% recovery for gel/sensors having pressure applied vs. ~25% recovery for gel/sensors not having pressure applied.

Using pressure to improve the interfacial contact between the hydrogel and the sensor substantially increased the sensitivity of the system, both in the speed of recovery and overall signal measured.

Experiments performed in support of the present invention have shown that improved "wetting" of the gel on the sensor (through storing of gel in contact with a sensor for an extended period of time, or pre-treatment of the sensor) improves contact and gives rise to higher sensitivity. However, it was not anticipated that the use of pressure to improve the interfacial contact between the hydrogel and the sensor would lead to improvements well beyond what was seen by improving the interface by these other means.

Correlation statistics from actual human studies have shown that the quality of the data was dramatically increased when using pressure treatment to improve the interfacial contact of the hydrogel with the sensor.

EXAMPLE 2

Figure 15:
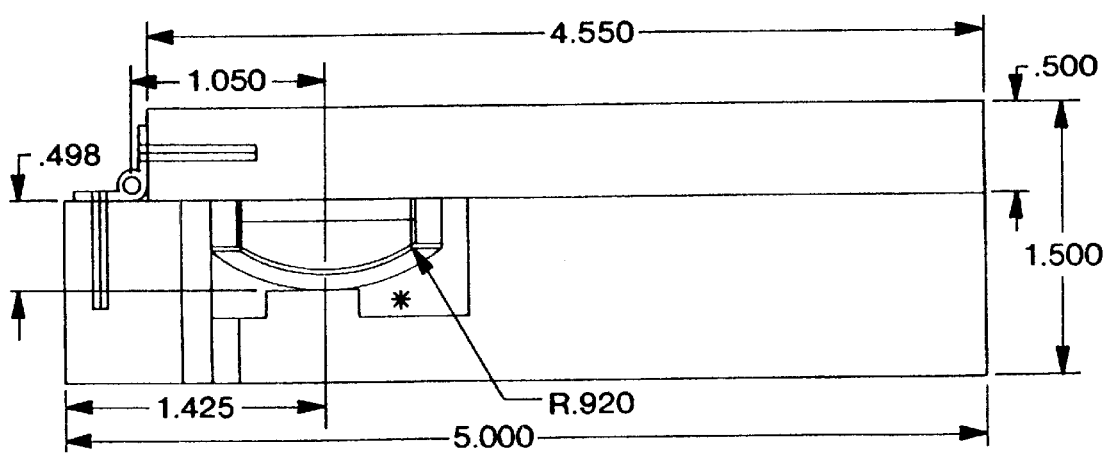
FIG. 15 presents a line drawing with appropriate dimensions (in inches) given for one embodiment of the press device of the present invention.

The experiment described in Example 1 was repeated using a press device having the dimensions shown in FIG. 15. The top of the press device was lifted and the collection/electrode assembly, having a total thickness of about 0.129 inches, was placed in the press device in an appropriate orientation (for general location refer to the Asterisk in FIG. 15). The top of the press was lowered, and pressure was applied sufficient to bring the first surface of the device (i.e., the top surface of the base) into contact with the second surface of the device (i.e., the bottom surface of the cover of the press device). This pressure was maintained for about 10 seconds at room temperature.

As was seen in Example 1, using pressure, in this case a mechanically generated pressure, to improve the interfacial contact between the hydrogel and the sensor substantially increased the sensitivity of the system, both in the speed of recovery and overall signal measured.

Although preferred embodiments of the subject invention have been described in some detail, it is understood that obvious variations can be made without departing from the spirit and the scope of the invention as defined by the appended claims.

What is claimed is:

1. A press device to apply mechanical force to improve contact between an ionically conductive gel and a sensor, comprising a press device having first and second surfaces, wherein
the first surface is conformed to hold a gel and sensor assembly, and
the second surface is conformed to contact the assembly such that the application of mechanical force to the first and second surfaces of the device brings the gel into contact with the sensor, wherein the amount of mechanical force that can be applied is lower than the amount of force that would cause unacceptable deformation of the gel, sensor, or assembly.

2. The press device of claim 1, which further comprises a sliding means to hold the first and second surfaces together.

3. The press device of claim 1, wherein applying said mechanical force is accomplished using roller means.

4. The press device of claim 1, wherein an end of the first surface is connected to an end of the second surfaces.

5. The press device of claim 4, wherein the end of the first surface is connected to the end of the second surfaces by hinge means.

6. The press device of claim 1, wherein the second surface is conformed by the addition of contacting means.

7. The press device of claim 6, wherein said contacting means are formed from an elastomeric material.

8. The press device of claim 7, wherein said elastomeric material is silicone or polyurethane.

9. The press device of claim 4, which further comprises a latching means to hold the first and second surfaces together.

10. The press device of claim 9, wherein said latching means are timed to release after a specified period.

11. A method of improving signal detection in a transdermal sampling device, said device employing an ionically conductive material in contact with a sensor, comprising
applying force to bring the ionically conductive material into contact with the sensor, wherein the amount of force applied is lower than the amount of force that would cause unacceptable damage to the conductive material or sensor,
wherein said force is mechanical pressure, and the mechanical pressure is applied by a press device, said press device comprising,
a first surface on which the tonically conductive material and sensor are placed, said ionically conductive material and sensor being functionally aligned: and,
a second surface which is conformed to contact the ionically conductive material and sensor in such a way as to apply a mechanical force that brings the ionically conductive material into contact with the sensor, where the amount of mechanical force applied is lower than the amount of force that would cause unacceptable deformation of the ionically conductive material or sensor.

12. The method of claim 11, wherein said ionically conductive material is a hydrogel.

13. The method of claim 11, wherein said press device further comprises a sliding means to hold the first and second surfaces together.

14. The method of claim 11, wherein applying said mechanical force is accomplished using roller means.

15. The method of claim 11, wherein the first and second surfaces are connected by a hinge means.

16. The method of claim 11, wherein the second surface is conformed by the addition of contacting means.

17. The method of claim 16, wherein said contacting means are formed from an elastomeric material.

18. The method of claim 17, wherein said elastomeric material is silicone or polyurethane.

19. The method of claim 15, which further comprises a latching means to hold the first and second surfaces together.

20. The method of claim 19, wherein said latching means are timed to release after a specified period.

* * * * *

UNITED STATES PATENT AND TRADEMARK OFFICE
CERTIFICATE OF CORRECTION

PATENT NO. : 6,398,562 B1
DATED : June 4, 2002
INVENTOR(S) : Michael J. Butler et al.

It is certified that error appears in the above-identified patent and that said Letters Patent is hereby corrected as shown below:

<u>Column 32,</u>
Line 4, "on which the tonically conductive" should be -- on which the ionically conductive --.

Signed and Sealed this

Twenty-third Day of July, 2002

*Attest:*

*Attesting Officer*

JAMES E. ROGAN
*Director of the United States Patent and Trademark Office*